US008070746B2

(12) United States Patent
Orton et al.

(10) Patent No.: US 8,070,746 B2
(45) Date of Patent: Dec. 6, 2011

(54) RADIOFREQUENCY FUSION OF CARDIAC TISSUE

(75) Inventors: E. Christopher Orton, Fort Collins, CO (US); Michael C. Moses, Boulder, CO (US); Amy Denham, Boulder, CO (US); Jeffrey Townsend, Loveland, CO (US)

(73) Assignee: TYCO Healthcare Group LP, Boulder, CO (US)

( * ) Notice: Subject to any disclaimer, the term of this patent is extended or adjusted under 35 U.S.C. 154(b) by 1229 days.

(21) Appl. No.: 11/807,251

(22) Filed: May 25, 2007

(65) Prior Publication Data

US 2008/0082100 A1 Apr. 3, 2008

Related U.S. Application Data

(60) Provisional application No. 60/848,959, filed on Oct. 3, 2006.

(51) Int. Cl.
*A61B 18/14* (2006.01)
(52) U.S. Cl. .................. 606/32; 606/51; 606/52
(58) Field of Classification Search .......... 606/32, 606/51, 52
See application file for complete search history.

(56) References Cited

U.S. PATENT DOCUMENTS

| 371,664 | A | 10/1887 | Brannan et al. |
|---|---|---|---|
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 1,822,330 | A | 9/1931 | Ainslie |
| 1,852,542 | A | 4/1932 | Sovatkin |
| 2,002,594 | A | 5/1935 | Wappler et al. |
| 2,011,169 | A | 8/1935 | Wappler |
| 2,031,682 | A | 2/1936 | Wappler et al. |
| 2,054,149 | A | 9/1936 | Wappler |
| 2,176,479 | A | 10/1939 | Willis |
| 2,305,156 | A | 4/1941 | Grubel |
| 2,279,753 | A | 4/1942 | Knopp |
| 2,327,353 | A | 8/1943 | Karle |
| 2,632,661 | A | 8/1948 | Cristofv |

(Continued)

FOREIGN PATENT DOCUMENTS

CA 2104423 2/1994

(Continued)

OTHER PUBLICATIONS

Int'l Search Report EP 06 020574.7 dated Sep. 21, 2007.

(Continued)

*Primary Examiner* — Lee Cohen

(57) ABSTRACT

A method for cardiac surgical intervention relies on sealing or fusing heart valve leaflets without requiring implanted materials such as sutures or staples. The method provides a forceps having at least one shaft and an end effector assembly attached thereto. The end effector assembly includes a pair of opposing jaw members configured to move from an open, spread position to a closed, grasping position; creating at least one opening in the patient for inserting the forceps therein; inserting through the opening and manipulating jaw members of the forceps to grasp a portion of a first heart valve leaflet and a portion of a second heart valve leaflet therebetween; activating the forceps to close the jaw members about the leaflet portions under a working pressure, applying radiofrequency energy to the jaw members to seal the portion of the first heart valve leaflet to the portion of the second heart valve leaflet.

8 Claims, 9 Drawing Sheets

U.S. PATENT DOCUMENTS

| | | |
|---|---|---|
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |

| | | | | | |
|---|---|---|---|---|---|
| 5,411,519 A | 5/1995 | Tovey et al. | 5,611,798 A | 3/1997 | Eggers |
| 5,411,520 A | 5/1995 | Nash et al. | 5,611,808 A | 3/1997 | Hossain et al. |
| 5,413,571 A | 5/1995 | Katsaros et al. | 5,611,813 A | 3/1997 | Lichtman |
| 5,415,656 A | 5/1995 | Tihon et al. | 5,620,415 A | 4/1997 | Lucey et al. |
| 5,415,657 A | 5/1995 | Taymor-Luria | 5,620,453 A | 4/1997 | Nallakrishnan |
| 5,422,567 A | 6/1995 | Matsunaga | 5,620,459 A | 4/1997 | Lichtman |
| 5,423,810 A | 6/1995 | Goble et al. | 5,624,452 A | 4/1997 | Yates |
| 5,425,690 A | 6/1995 | Chang | 5,626,578 A | 5/1997 | Tihon |
| 5,425,739 A | 6/1995 | Jessen | 5,626,609 A | 5/1997 | Zvenyatsky et al. |
| 5,429,616 A | 7/1995 | Schaffer | 5,630,833 A | 5/1997 | Katsaros et al. |
| 5,431,672 A | 7/1995 | Cote et al. | 5,637,110 A | 6/1997 | Pennybacker et al. |
| 5,431,674 A | 7/1995 | Basile et al. | 5,638,003 A | 6/1997 | Hall |
| 5,437,292 A | 8/1995 | Kipshidze et al. | 5,643,294 A | 7/1997 | Tovey et al. |
| 5,438,302 A | 8/1995 | Goble | 5,647,869 A | 7/1997 | Goble et al. |
| 5,439,478 A | 8/1995 | Palmer | 5,647,871 A | 7/1997 | Levine et al. |
| 5,441,517 A | 8/1995 | Kensey et al. | 5,649,959 A | 7/1997 | Hannam et al. |
| 5,443,463 A | 8/1995 | Stern et al. | 5,655,650 A | 8/1997 | Naitou |
| 5,443,464 A | 8/1995 | Russell et al. | 5,658,281 A | 8/1997 | Heard |
| 5,443,480 A | 8/1995 | Jacobs et al. | D384,413 S | 9/1997 | Zlock et al. |
| 5,445,638 A | 8/1995 | Rydell et al. | 5,662,667 A | 9/1997 | Knodel |
| 5,445,658 A | 8/1995 | Durrfeld et al. | 5,665,100 A | 9/1997 | Yoon |
| 5,449,480 A | 9/1995 | Kuriya et al. | 5,667,526 A | 9/1997 | Levin |
| 5,451,224 A | 9/1995 | Goble et al. | 5,674,220 A | 10/1997 | Fox et al. |
| 5,454,823 A | 10/1995 | Richardson et al. | 5,674,229 A | 10/1997 | Tovey et al. |
| 5,454,827 A | 10/1995 | Aust et al. | 5,681,282 A | 10/1997 | Eggers et al. |
| 5,456,684 A | 10/1995 | Schmidt et al. | 5,688,270 A | 11/1997 | Yates et al. |
| 5,458,598 A | 10/1995 | Feinberg et al. | 5,690,652 A | 11/1997 | Wurster et al. |
| 5,460,629 A | 10/1995 | Shlain et al. | 5,690,653 A | 11/1997 | Richardson et al. |
| 5,461,765 A | 10/1995 | Linden et al. | 5,693,051 A | 12/1997 | Schulze et al. |
| 5,462,546 A | 10/1995 | Rydell | 5,693,920 A | 12/1997 | Maeda |
| 5,472,442 A | 12/1995 | Klicek | 5,695,522 A | 12/1997 | LeMaire, III et al. |
| 5,472,443 A | 12/1995 | Cordis et al. | 5,700,261 A | 12/1997 | Brinkerhoff |
| 5,478,351 A | 12/1995 | Meade et al. | 5,700,270 A | 12/1997 | Peyser et al. |
| 5,480,406 A | 1/1996 | Nolan et al. | 5,702,390 A | 12/1997 | Austin et al. |
| 5,480,409 A | 1/1996 | Riza | 5,707,369 A | 1/1998 | Vaitekunas et al. |
| 5,484,436 A | 1/1996 | Eggers et al. | 5,709,680 A | 1/1998 | Yates et al. |
| 5,496,312 A | 3/1996 | Klicek | 5,716,366 A | 2/1998 | Yates |
| 5,496,317 A | 3/1996 | Goble et al. | 5,720,744 A | 2/1998 | Eggleston et al. |
| 5,496,347 A | 3/1996 | Hashiguchi et al. | 5,722,421 A | 3/1998 | Francese et al. |
| 5,499,997 A | 3/1996 | Sharpe et al. | 5,725,536 A | 3/1998 | Oberlin et al. |
| 5,509,922 A | 4/1996 | Aranyi et al. | 5,727,428 A | 3/1998 | LeMaire, III et al. |
| 5,514,134 A | 5/1996 | Rydell et al. | 5,735,848 A | 4/1998 | Yates et al. |
| 5,527,313 A | 6/1996 | Scott et al. | 5,743,906 A | 4/1998 | Parins et al. |
| 5,528,833 A | 6/1996 | Sakuma | 5,752,973 A | 5/1998 | Kieturakis |
| 5,529,067 A | 6/1996 | Larsen et al. | 5,755,717 A | 5/1998 | Yates et al. |
| 5,531,744 A | 7/1996 | Nardella et al. | 5,759,188 A | 6/1998 | Yoon |
| 5,536,251 A | 7/1996 | Evard et al. | 5,766,130 A | 6/1998 | Selmonosky |
| 5,540,684 A | 7/1996 | Hassler, Jr. | 5,766,166 A | 6/1998 | Hooven |
| 5,540,685 A | 7/1996 | Parins et al. | 5,766,170 A | 6/1998 | Eggers |
| 5,540,706 A | 7/1996 | Aust et al. | 5,766,196 A | 6/1998 | Griffiths |
| 5,540,715 A | 7/1996 | Katsaros et al. | 5,769,849 A | 6/1998 | Eggers |
| 5,542,945 A | 8/1996 | Fritzsch | 5,772,655 A | 6/1998 | Bauer et al. |
| 5,558,671 A | 9/1996 | Yates | 5,772,670 A | 6/1998 | Brosa |
| 5,558,672 A | 9/1996 | Edwards et al. | 5,776,128 A | 7/1998 | Eggers |
| 5,562,619 A | 10/1996 | Mirarchi et al. | 5,776,130 A | 7/1998 | Buysse et al. |
| 5,562,699 A | 10/1996 | Heimberger et al. | 5,779,646 A | 7/1998 | Koblish et al. |
| 5,562,720 A | 10/1996 | Stern et al. | 5,779,701 A | 7/1998 | McBrayer et al. |
| 5,564,615 A | 10/1996 | Bishop et al. | H1745 H | 8/1998 | Paraschac |
| 5,569,241 A | 10/1996 | Edwardds | 5,792,137 A | 8/1998 | Carr et al. |
| 5,569,243 A | 10/1996 | Kortenbach et al. | 5,792,165 A | 8/1998 | Klieman et al. |
| 5,571,100 A | 11/1996 | Goble et al. | 5,792,177 A | 8/1998 | Kaseda |
| 5,573,424 A | 11/1996 | Poppe | 5,797,537 A | 8/1998 | Oberlin et al. |
| 5,573,534 A | 11/1996 | Stone | 5,797,927 A | 8/1998 | Yoon |
| 5,573,535 A | 11/1996 | Viklund | 5,797,938 A | 8/1998 | Paraschac et al. |
| 5,575,799 A | 11/1996 | Bolanos et al. | 5,797,941 A | 8/1998 | Schulze et al. |
| 5,575,805 A | 11/1996 | Li | 5,797,958 A | 8/1998 | Yoon |
| 5,578,052 A | 11/1996 | Koros et al. | 5,800,449 A | 9/1998 | Wales |
| 5,579,781 A | 12/1996 | Cooke | 5,807,393 A | 9/1998 | Williamson, IV et al. |
| 5,582,611 A | 12/1996 | Tsukagoshi et al. | 5,810,764 A | 9/1998 | Eggers et al. |
| 5,582,617 A | 12/1996 | Klieman et al. | 5,810,805 A | 9/1998 | Sutcu et al. |
| 5,585,896 A | 12/1996 | Yamazaki et al. | 5,810,808 A | 9/1998 | Eggers |
| 5,590,570 A | 1/1997 | LeMaire, III et al. | 5,810,811 A | 9/1998 | Yates et al. |
| 5,591,181 A | 1/1997 | Stone et al. | 5,810,877 A | 9/1998 | Roth et al. |
| 5,597,107 A | 1/1997 | Knodel et al. | 5,814,043 A | 9/1998 | Shapeton |
| 5,601,224 A | 2/1997 | Bishop et al. | 5,814,054 A | 9/1998 | Kortenbach et al. |
| 5,601,601 A | 2/1997 | Tal et al. | 5,817,093 A | 10/1998 | Williamson, IV et al. |
| 5,601,641 A | 2/1997 | Stephens | 5,817,119 A | 10/1998 | Klieman et al. |
| 5,603,711 A | 2/1997 | Parins et al. | 5,820,630 A | 10/1998 | Lind |
| 5,603,723 A | 2/1997 | Aranyi et al. | 5,824,978 A | 10/1998 | Karasik et al. |

| | | | | | | |
|---|---|---|---|---|---|---|
| 5,827,271 | A | 10/1998 | Buysse et al. | 6,096,037 | A | 8/2000 | Mulier et al. |
| 5,827,279 | A | 10/1998 | Hughett et al. | 6,099,550 | A | 8/2000 | Yoon |
| 5,827,281 | A | 10/1998 | Levin | 6,102,909 | A | 8/2000 | Chen et al. |
| 5,827,323 | A | 10/1998 | Klieman et al. | 6,106,542 | A | 8/2000 | Toybin et al. |
| 5,827,548 | A | 10/1998 | Lavallee et al. | 6,110,171 | A | 8/2000 | Rydell |
| 5,833,690 | A | 11/1998 | Yates et al. | 6,113,596 | A | 9/2000 | Hooven et al. |
| 5,843,080 | A | 12/1998 | Fleenor et al. | 6,113,598 | A | 9/2000 | Baker |
| 5,849,022 | A | 12/1998 | Sakashita et al. | 6,117,158 | A | 9/2000 | Measamer et al. |
| 5,853,412 | A | 12/1998 | Mayenberger | 6,122,549 | A | 9/2000 | Sharkey et al. |
| 5,859,527 | A | 1/1999 | Cook | 6,123,701 | A | 9/2000 | Nezhat |
| 5,860,976 | A | 1/1999 | Billings et al. | H1904 | H | 10/2000 | Yates et al. |
| 5,876,401 | A | 3/1999 | Schulze et al. | 6,126,658 | A | 10/2000 | Baker |
| 5,876,412 | A | 3/1999 | Piraka | 6,126,665 | A | 10/2000 | Yoon |
| 5,882,567 | A | 3/1999 | Cavallaro et al. | 6,139,563 | A | 10/2000 | Cosgrove, III et al. |
| 5,891,141 | A | 4/1999 | Rydell | 6,143,005 | A | 11/2000 | Yoon et al. |
| 5,891,142 | A | 4/1999 | Eggers et al. | 6,152,923 | A | 11/2000 | Ryan |
| 5,893,863 | A | 4/1999 | Yoon | 6,162,220 | A | 12/2000 | Nezhat |
| 5,893,875 | A | 4/1999 | O'Connor et al. | 6,171,316 | B1 | 1/2001 | Kovac et al. |
| 5,893,877 | A | 4/1999 | Gampp, Jr. et al. | 6,174,309 | B1 | 1/2001 | Wrublewski et al. |
| 5,897,563 | A | 4/1999 | Yoon et al. | 6,178,628 | B1 | 1/2001 | Clemens et al. |
| 5,902,301 | A | 5/1999 | Olig | 6,179,834 | B1 | 1/2001 | Buysse et al. |
| 5,906,630 | A | 5/1999 | Anderhub et al. | 6,179,837 | B1 | 1/2001 | Hooven |
| 5,908,420 | A | 6/1999 | Parins et al. | 6,183,467 | B1 | 2/2001 | Shapeton et al. |
| 5,908,432 | A | 6/1999 | Pan | 6,187,003 | B1 | 2/2001 | Buysse et al. |
| 5,911,719 | A | 6/1999 | Eggers | 6,190,386 | B1 | 2/2001 | Rydell |
| 5,913,874 | A | 6/1999 | Berns et al. | 6,190,400 | B1 | 2/2001 | Vandemoer et al. |
| 5,921,916 | A | 7/1999 | Aeikens et al. | 6,193,718 | B1 | 2/2001 | Kortenbach et al. |
| 5,921,984 | A | 7/1999 | Sutcu et al. | 6,206,876 | B1 | 3/2001 | Levine et al. |
| 5,925,043 | A | 7/1999 | Kumar et al. | 6,206,877 | B1 | 3/2001 | Kese et al. |
| 5,928,136 | A | 7/1999 | Barry | 6,206,893 | B1 | 3/2001 | Klein et al. |
| 5,935,126 | A | 8/1999 | Riza | 6,214,028 | B1 | 4/2001 | Yoon et al. |
| 5,941,869 | A | 8/1999 | Patterson et al. | 6,217,602 | B1 | 4/2001 | Redmon |
| 5,944,718 | A | 8/1999 | Dafforn et al. | 6,217,615 | B1 | 4/2001 | Sioshansi et al. |
| 5,951,546 | A | 9/1999 | Lorentzen | 6,221,039 | B1 | 4/2001 | Durgin et al. |
| 5,951,549 | A | 9/1999 | Richardson et al. | 6,223,100 | B1 | 4/2001 | Green |
| 5,954,720 | A | 9/1999 | Wilson et al. | 6,224,593 | B1 | 5/2001 | Ryan et al. |
| 5,954,731 | A | 9/1999 | Yoon | 6,224,614 | B1 | 5/2001 | Yoon |
| 5,954,733 | A | 9/1999 | Yoon | 6,228,080 | B1 | 5/2001 | Gines |
| 5,957,923 | A | 9/1999 | Hahnen et al. | 6,228,083 | B1 | 5/2001 | Lands et al. |
| 5,957,937 | A | 9/1999 | Yoon | 6,248,124 | B1 | 6/2001 | Pedros et al. |
| 5,960,544 | A | 10/1999 | Beyers | 6,248,944 | B1 | 6/2001 | Ito |
| 5,961,514 | A | 10/1999 | Long et al. | 6,261,307 | B1 | 7/2001 | Yoon et al. |
| 5,964,758 | A | 10/1999 | Dresden | 6,267,761 | B1 | 7/2001 | Ryan |
| 5,976,132 | A | 11/1999 | Morris | 6,270,497 | B1 | 8/2001 | Sekino et al. |
| 5,984,932 | A | 11/1999 | Yoon | 6,270,508 | B1 | 8/2001 | Klieman et al. |
| 5,984,938 | A | 11/1999 | Yoon | 6,273,887 | B1 | 8/2001 | Yamauchi et al. |
| 5,984,939 | A | 11/1999 | Yoon | 6,277,117 | B1 | 8/2001 | Tetzlaff et al. |
| 5,989,277 | A | 11/1999 | LeMaire, III et al. | 6,280,458 | B1 | 8/2001 | Boche et al. |
| 5,993,466 | A | 11/1999 | Yoon | 6,283,961 | B1 | 9/2001 | Underwood et al. |
| 5,993,467 | A | 11/1999 | Yoon | D449,886 | S | 10/2001 | Tetzlaff et al. |
| 5,997,565 | A | 12/1999 | Inoue | 6,298,550 | B1 | 10/2001 | Kirwan |
| 6,004,332 | A | 12/1999 | Yoon et al. | 6,302,424 | B1 | 10/2001 | Gisinger et al. |
| 6,004,335 | A | 12/1999 | Vaitekunas et al. | 6,319,262 | B1 | 11/2001 | Bates et al. |
| 6,010,516 | A | 1/2000 | Hulka et al. | 6,319,451 | B1 | 11/2001 | Brune |
| 6,017,358 | A | 1/2000 | Yoon et al. | 6,322,561 | B1 | 11/2001 | Eggers et al. |
| 6,021,693 | A | 2/2000 | Feng-Sing | 6,322,580 | B1 | 11/2001 | Kanner |
| 6,024,741 | A | 2/2000 | Williamson et al. | 6,325,795 | B1 | 12/2001 | Lindemann et al. |
| 6,024,743 | A | 2/2000 | Edwards | 6,334,860 | B1 | 1/2002 | Dorn |
| 6,024,744 | A | 2/2000 | Kese et al. | 6,334,861 | B1 | 1/2002 | Chandler et al. |
| 6,027,522 | A | 2/2000 | Palmer | 6,345,532 | B1 | 2/2002 | Coudray et al. |
| 6,030,384 | A | 2/2000 | Nezhat | 6,350,264 | B1 | 2/2002 | Hooven |
| 6,033,399 | A | 3/2000 | Gines | 6,352,536 | B1 | 3/2002 | Buysse et al. |
| 6,039,733 | A | 3/2000 | Buysse et al. | 6,358,249 | B1 | 3/2002 | Chen et al. |
| 6,041,679 | A | 3/2000 | Slater et al. | 6,358,259 | B1 | 3/2002 | Swain et al. |
| 6,050,996 | A | 4/2000 | Schmaltz et al. | 6,358,268 | B1 | 3/2002 | Hunt et al. |
| 6,053,914 | A | 4/2000 | Eggers et al. | 6,364,879 | B1 | 4/2002 | Chen et al. |
| 6,053,933 | A | 4/2000 | Balazs et al. | D457,958 | S | 5/2002 | Dycus et al. |
| D424,694 | S | 5/2000 | Tetzlaff et al. | D457,959 | S | 5/2002 | Tetzlaff et al. |
| D425,201 | S | 5/2000 | Tetzlaff et al. | 6,387,094 | B1 | 5/2002 | Eitenmuller |
| 6,059,782 | A | 5/2000 | Novak et al. | 6,391,035 | B1 | 5/2002 | Appleby et al. |
| 6,066,139 | A | 5/2000 | Ryan et al. | 6,398,779 | B1 | 6/2002 | Buysse et al. |
| 6,074,386 | A | 6/2000 | Goble et al. | 6,402,747 | B1 | 6/2002 | Lindemann et al. |
| 6,077,287 | A | 6/2000 | Taylor et al. | 6,409,728 | B1 | 6/2002 | Ehr et al. |
| 6,080,180 | A | 6/2000 | Yoon et al. | H2037 | H | 7/2002 | Yates et al. |
| RE36,795 | E | 7/2000 | Rydell | 6,419,675 | B1 | 7/2002 | Gallo, Sr. |
| 6,083,223 | A | 7/2000 | Baker | 6,425,896 | B1 | 7/2002 | Baltschun et al. |
| 6,086,586 | A | 7/2000 | Hooven | 6,432,112 | B2 | 8/2002 | Brock et al. |
| 6,086,601 | A | 7/2000 | Yoon | 6,440,144 | B1 | 8/2002 | Bacher |
| 6,090,107 | A | 7/2000 | Borgmeier et al. | 6,443,952 | B1 | 9/2002 | Mulier et al. |

| | | | |
|---|---|---|---|
| 6,443,970 B1 | 9/2002 | Schulze et al. | |
| 6,451,018 B1 | 9/2002 | Lands et al. | |
| 6,458,125 B1 | 10/2002 | Cosmescu | |
| 6,458,128 B1 | 10/2002 | Schulze | |
| 6,458,130 B1 | 10/2002 | Frazier et al. | |
| 6,461,352 B2 | 10/2002 | Morgan et al. | |
| 6,461,368 B2 | 10/2002 | Fogarty et al. | |
| 6,464,701 B1 | 10/2002 | Hooven et al. | |
| 6,464,702 B2* | 10/2002 | Schulze et al. | |
| 6,464,704 B2* | 10/2002 | Schmaltz et al. | |
| 6,485,489 B2 | 11/2002 | Teirstein et al. | |
| 6,494,888 B1 | 12/2002 | Laufer et al. | |
| 6,500,176 B1 | 12/2002 | Truckai et al. | |
| 6,506,196 B1 | 1/2003 | Laufer | |
| 6,508,815 B1 | 1/2003 | Strul et al. | |
| 6,511,480 B1* | 1/2003 | Tetzlaff et al. | |
| 6,514,215 B1 | 2/2003 | Ouchi | |
| 6,514,252 B2 | 2/2003 | Nezhat et al. | |
| 6,517,539 B1 | 2/2003 | Smith et al. | |
| 6,527,771 B1* | 3/2003 | Weadock et al. | |
| 6,533,784 B2 | 3/2003 | Truckai et al. | |
| 6,545,239 B2 | 4/2003 | Spedale et al. | |
| 6,558,385 B1 | 5/2003 | McClurken et al. | |
| 6,562,037 B2 | 5/2003 | Paton et al. | |
| 6,569,105 B1 | 5/2003 | Kortenbach et al. | |
| 6,582,450 B2 | 6/2003 | Ouchi | |
| 6,585,735 B1* | 7/2003 | Frazier et al. | 606/51 |
| 6,602,252 B2* | 8/2003 | Mollenauer | |
| 6,605,790 B2 | 8/2003 | Yoshida | |
| 6,616,658 B2 | 9/2003 | Ineson | |
| 6,616,661 B2 | 9/2003 | Wellman et al. | |
| 6,620,161 B2* | 9/2003 | Schulze et al. | |
| 6,620,184 B2 | 9/2003 | De Laforcade et al. | |
| 6,626,901 B1* | 9/2003 | Treat et al. | |
| 6,629,534 B1* | 10/2003 | St. Goar et al. | 128/898 |
| 6,638,287 B2 | 10/2003 | Danitz et al. | |
| 6,641,595 B1* | 11/2003 | Moran et al. | |
| 6,652,514 B2 | 11/2003 | Ellman et al. | |
| 6,652,521 B2* | 11/2003 | Schulze | |
| 6,656,175 B2 | 12/2003 | Francischelli et al. | |
| 6,656,177 B2* | 12/2003 | Truckai et al. | |
| 6,660,072 B2* | 12/2003 | Chatterjee | |
| 6,663,639 B1 | 12/2003 | Laufer et al. | |
| 6,663,641 B1 | 12/2003 | Kovac et al. | |
| 6,666,854 B1 | 12/2003 | Lange | |
| 6,669,696 B2* | 12/2003 | Bacher et al. | |
| 6,673,092 B1 | 1/2004 | Bacher | |
| 6,676,660 B2 | 1/2004 | Wampler et al. | |
| 6,676,676 B2 | 1/2004 | Danitz et al. | |
| 6,679,882 B1 | 1/2004 | Kornerup | |
| 6,682,527 B2* | 1/2004 | Strul | |
| 6,682,528 B2* | 1/2004 | Frazier et al. | |
| 6,685,724 B1* | 2/2004 | Haluck | |
| 6,689,131 B2 | 2/2004 | McClurken | |
| 6,692,445 B2 | 2/2004 | Roberts et al. | |
| 6,693,246 B1 | 2/2004 | Rudolph et al. | |
| 6,695,840 B2* | 2/2004 | Schulze | |
| 6,702,810 B2* | 3/2004 | McClurken et al. | |
| 6,723,092 B2 | 4/2004 | Brown et al. | |
| 6,726,068 B2* | 4/2004 | Miller | |
| 6,726,686 B2* | 4/2004 | Buysse et al. | |
| 6,726,694 B2 | 4/2004 | Blatter et al. | |
| 6,733,498 B2* | 5/2004 | Paton et al. | |
| 6,736,813 B2 | 5/2004 | Yamauchi et al. | |
| 6,743,229 B2* | 6/2004 | Buysse et al. | |
| 6,743,230 B2 | 6/2004 | Lutze et al. | |
| 6,743,239 B1 | 6/2004 | Kuehn et al. | |
| 6,743,240 B2 | 6/2004 | Smith et al. | |
| 6,755,843 B2 | 6/2004 | Chung et al. | |
| 6,756,553 B1 | 6/2004 | Yamaguchi et al. | |
| 6,757,977 B2 | 7/2004 | Dambal et al. | |
| D493,888 S | 8/2004 | Reschke | |
| 6,770,072 B1* | 8/2004 | Truckai et al. | |
| 6,773,409 B2 | 8/2004 | Truckai et al. | |
| 6,773,432 B1 | 8/2004 | Clayman et al. | |
| 6,773,434 B2* | 8/2004 | Ciarrocca | |
| 6,773,441 B1 | 8/2004 | Laufer et al. | |
| 6,775,575 B2 | 8/2004 | Bommannan et al. | |
| 6,776,780 B2* | 8/2004 | Mulier et al. | |
| 6,786,905 B2 | 9/2004 | Swanson et al. |
| 6,790,217 B2* | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2* | 10/2004 | Truckai et al. |
| 6,808,525 B2 | 10/2004 | Latterell et al. |
| D499,181 S | 11/2004 | Dycus et al. |
| 6,818,000 B2* | 11/2004 | Muller et al. |
| 6,821,285 B2 | 11/2004 | Laufer et al. |
| 6,835,200 B2 | 12/2004 | Laufer et al. |
| 6,857,357 B2 | 2/2005 | Fujii |
| 6,860,880 B2* | 3/2005 | Treat et al. |
| 6,887,240 B1* | 5/2005 | Lands et al. |
| 6,889,116 B2 | 5/2005 | Jinno |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,953,430 B2 | 10/2005 | Kodooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |

| | | | | | | |
|---|---|---|---|---|---|---|
| 7,156,846 B2 | 1/2007 | Dycus et al. | | 2003/0158549 A1 | 8/2003 | Swanson |
| 7,160,298 B2 | 1/2007 | Lawes et al. | | 2003/0171747 A1 | 9/2003 | Kanehira et al. |
| 7,160,299 B2 | 1/2007 | Baily | | 2003/0181910 A1 | 9/2003 | Dycus et al. |
| 7,169,146 B2 | 1/2007 | Truckai et al. | | 2003/0216732 A1 | 11/2003 | Truckai et al. |
| 7,179,255 B2 | 2/2007 | Lettice et al. | | 2003/0220637 A1 | 11/2003 | Truckai et al. |
| 7,179,258 B2 | 2/2007 | Buysse et al. | | 2003/0229344 A1 | 12/2003 | Dycus et al. |
| 7,195,631 B2 | 3/2007 | Dumbauld | | 2003/0236325 A1 | 12/2003 | Bonora |
| D541,418 S | 4/2007 | Schechter et al. | | 2003/0236518 A1 | 12/2003 | Marchitto et al. |
| 7,207,990 B2 | 4/2007 | Lands et al. | | 2004/0030330 A1 | 2/2004 | Brassell et al. |
| D541,938 S | 5/2007 | Kerr et al. | | 2004/0030332 A1 | 2/2004 | Knowlton et al. |
| 7,223,264 B2 | 5/2007 | Daniel et al. | | 2004/0049185 A1 | 3/2004 | Latterell et al. |
| 7,223,265 B2 | 5/2007 | Keppel | | 2004/0064151 A1 | 4/2004 | Mollenauer |
| 7,232,440 B2 | 6/2007 | Dumbauld et al. | | 2004/0073238 A1 | 4/2004 | Makower |
| 7,241,288 B2 | 7/2007 | Braun | | 2004/0073256 A1 | 4/2004 | Marchitto et al. |
| 7,241,296 B2 | 7/2007 | Buysse et al. | | 2004/0078035 A1 | 4/2004 | Kanehira et al. |
| 7,244,257 B2 | 7/2007 | Podjahsky et al. | | 2004/0082952 A1 | 4/2004 | Dycus et al. |
| 7,246,734 B2 | 7/2007 | Shelton, IV | | 2004/0087943 A1 | 5/2004 | Dycus et al. |
| 7,248,944 B2 | 7/2007 | Green | | 2004/0115296 A1 | 6/2004 | Duffin |
| 7,252,667 B2 | 8/2007 | Moses et al. | | 2004/0116924 A1 | 6/2004 | Dycus et al. |
| 7,255,697 B2 | 8/2007 | Dycus et al. | | 2004/0116979 A1 | 6/2004 | Truckai et al. |
| 7,267,677 B2 | 9/2007 | Johnson et al. | | 2004/0122423 A1 | 6/2004 | Dycus et al. |
| 7,270,660 B2 | 9/2007 | Ryan | | 2004/0143263 A1 | 7/2004 | Schechter et al. |
| 7,270,664 B2 | 9/2007 | Johnson et al. | | 2004/0148035 A1 | 7/2004 | Barrett et al. |
| 7,276,068 B2 | 10/2007 | Johnson et al. | | 2004/0162557 A1 | 8/2004 | Tetzlaff et al. |
| 7,300,435 B2 | 11/2007 | Wham et al. | | 2004/0193153 A1 | 9/2004 | Sarter et al. |
| 7,303,557 B2 | 12/2007 | Wham et al. | | 2004/0199181 A1 | 10/2004 | Knodel et al. |
| 7,311,709 B2 | 12/2007 | Truckai et al. | | 2004/0210282 A1 | 10/2004 | Flock et al. |
| 7,314,471 B2 | 1/2008 | Holman | | 2004/0224590 A1 | 11/2004 | Rawa et al. |
| 7,318,823 B2 | 1/2008 | Sharps et al. | | 2004/0230189 A1 | 11/2004 | Keppel |
| 7,329,256 B2 | 2/2008 | Johnson et al. | | 2004/0236326 A1 | 11/2004 | Schulze et al. |
| 7,329,257 B2 | 2/2008 | Kanehira et al. | | 2004/0243125 A1 | 12/2004 | Dycus et al. |
| D564,662 S | 3/2008 | Moses et al. | | 2004/0249371 A1 | 12/2004 | Dycus et al. |
| 7,338,526 B2 | 3/2008 | Steinberg | | 2004/0249374 A1 | 12/2004 | Tetzlaff et al. |
| 7,342,754 B2 | 3/2008 | Fitzgerald et al. | | 2004/0260281 A1 | 12/2004 | Baxter, III et al. |
| 7,344,268 B2 | 3/2008 | Jigamian | | 2005/0004564 A1 | 1/2005 | Wham et al. |
| D567,943 S | 4/2008 | Moses et al. | | 2005/0004569 A1 | 1/2005 | Witt et al. |
| 7,367,976 B2 | 5/2008 | Lawes et al. | | 2005/0021025 A1 | 1/2005 | Buysse et al. |
| 7,377,920 B2 | 5/2008 | Buysse et al. | | 2005/0021027 A1 | 1/2005 | Shields et al. |
| 7,384,420 B2 | 6/2008 | Dycus et al. | | 2005/0033278 A1 | 2/2005 | McClurken et al. |
| 7,384,421 B2 | 6/2008 | Hushka | | 2005/0059934 A1 | 3/2005 | Wenchell et al. |
| 7,396,336 B2 | 7/2008 | Orszulak et al. | | 2005/0096645 A1 | 5/2005 | Wellman et al. |
| D575,395 S | 8/2008 | Hushka | | 2005/0101951 A1 | 5/2005 | Wham et al. |
| D575,401 S | 8/2008 | Hixson et al. | | 2005/0101952 A1 | 5/2005 | Lands et al. |
| 7,435,249 B2 | 10/2008 | Buysse et al. | | 2005/0113818 A1 | 5/2005 | Sartor et al. |
| 7,442,193 B2 | 10/2008 | Shields et al. | | 2005/0113819 A1 | 5/2005 | Wham et al. |
| 7,442,194 B2 | 10/2008 | Dumbauld et al. | | 2005/0113826 A1 | 5/2005 | Johnson et al. |
| 7,445,621 B2 | 11/2008 | Dumbauld et al. | | 2005/0113828 A1 | 5/2005 | Shields et al. |
| 7,458,972 B2 | 12/2008 | Keppel | | 2005/0149017 A1 | 7/2005 | Dycus |
| 7,473,253 B2 | 1/2009 | Dycus et al. | | 2005/0149151 A1 | 7/2005 | Orszulak et al. |
| 7,481,810 B2 | 1/2009 | Dumbauld et al. | | 2005/0154387 A1 | 7/2005 | Moses et al. |
| 7,487,780 B2 | 2/2009 | Hooven | | 2005/0187547 A1 | 8/2005 | Sugi |
| 7,491,201 B2 | 2/2009 | Shields et al. | | 2005/0197659 A1 | 9/2005 | Bahney |
| 7,491,202 B2 | 2/2009 | Odom et al. | | 2005/0203504 A1 | 9/2005 | Wham et al. |
| 7,500,975 B2 | 3/2009 | Cunningham et al. | | 2005/0240179 A1 | 10/2005 | Buysse et al. |
| 7,510,556 B2 | 3/2009 | Nguyen et al. | | 2006/0052778 A1 | 3/2006 | Chapman et al. |
| 7,513,898 B2 | 4/2009 | Johnson et al. | | 2006/0052779 A1 | 3/2006 | Hammill |
| 7,540,872 B2 | 6/2009 | Schechter et al. | | 2006/0064085 A1 | 3/2006 | Schechter et al. |
| 7,549,995 B2 | 6/2009 | Schultz | | 2006/0064086 A1 | 3/2006 | Odom |
| 7,553,312 B2 | 6/2009 | Tetzlaff et al. | | 2006/0074417 A1 | 4/2006 | Cunningham et al. |
| 7,628,792 B2 * | 12/2009 | Guerra ............... 606/51 | | 2006/0079888 A1 | 4/2006 | Mulier et al. |
| 2002/0013583 A1 | 1/2002 | Camran et al. | | 2006/0079890 A1 | 4/2006 | Guerra |
| 2002/0049442 A1 | 4/2002 | Roberts et al. | | 2006/0079891 A1 | 4/2006 | Arts et al. |
| 2002/0099372 A1 | 7/2002 | Schulze et al. | | 2006/0079933 A1 | 4/2006 | Hushka et al. |
| 2002/0107517 A1 | 8/2002 | Witt et al. | | 2006/0084973 A1 | 4/2006 | Hushka |
| 2002/0111624 A1 | 8/2002 | Witt et al. | | 2006/0089670 A1 | 4/2006 | Hushka |
| 2002/0188294 A1 | 12/2002 | Couture et al. | | 2006/0116675 A1 | 6/2006 | McClurken et al. |
| 2003/0014052 A1 | 1/2003 | Buysse et al. | | 2006/0129146 A1 | 6/2006 | Dycus et al. |
| 2003/0014053 A1 | 1/2003 | Nguyen et al. | | 2006/0167450 A1 | 7/2006 | Johnson et al. |
| 2003/0018331 A1 | 1/2003 | Dycus et al. | | 2006/0167452 A1 | 7/2006 | Moses et al. |
| 2003/0018332 A1 | 1/2003 | Schmaltz et al. | | 2006/0173452 A1 | 8/2006 | Buysse et al. |
| 2003/0032956 A1 | 2/2003 | Lands et al. | | 2006/0189980 A1 | 8/2006 | Johnson et al. |
| 2003/0069570 A1 | 4/2003 | Witzel et al. | | 2006/0189981 A1 | 8/2006 | Dycus et al. |
| 2003/0069571 A1 | 4/2003 | Treat et al. | | 2006/0190035 A1 | 8/2006 | Hushka et al. |
| 2003/0078578 A1 | 4/2003 | Truckai et al. | | 2006/0217709 A1 | 9/2006 | Couture et al. |
| 2003/0109875 A1 | 6/2003 | Tetzlaff et al. | | 2006/0224158 A1 | 10/2006 | Odom et al. |
| 2003/0114851 A1 | 6/2003 | Truckai et al. | | 2006/0229666 A1 | 10/2006 | Suzuki et al. |
| 2003/0139741 A1 | 7/2003 | Goble et al. | | 2006/0253126 A1 | 11/2006 | Bjerken et al. |
| 2003/0139742 A1 | 7/2003 | Wampler et al. | | 2006/0259036 A1 | 11/2006 | Tetzlaff et al. |
| 2003/0158548 A1 | 8/2003 | Phan et al. | | 2006/0264922 A1 | 11/2006 | Sartor et al. |

| | | | |
|---|---|---|---|
| 2006/0264931 A1 | 11/2006 | Chapman et al. | |
| 2006/0283093 A1 | 12/2006 | Petrovic et al. | |
| 2006/0287641 A1 | 12/2006 | Perlin | |
| 2007/0016182 A1 | 1/2007 | Lipson et al. | |
| 2007/0016187 A1 | 1/2007 | Weinberg et al. | |
| 2007/0043352 A1 | 2/2007 | Garrison et al. | |
| 2007/0043353 A1 | 2/2007 | Dycus et al. | |
| 2007/0060919 A1 | 3/2007 | Isaacson et al. | |
| 2007/0062017 A1 | 3/2007 | Dycus et al. | |
| 2007/0074807 A1 | 4/2007 | Guerra | |
| 2007/0078456 A1 | 4/2007 | Dumbauld et al. | |
| 2007/0078458 A1 | 4/2007 | Dumbauld et al. | |
| 2007/0078459 A1 | 4/2007 | Johnson et al. | |
| 2007/0088356 A1 | 4/2007 | Moses et al. | |
| 2007/0106295 A1 | 5/2007 | Garrison et al. | |
| 2007/0106297 A1 | 5/2007 | Dumbauld et al. | |
| 2007/0118111 A1 | 5/2007 | Weinberg | |
| 2007/0118115 A1 | 5/2007 | Artale et al. | |
| 2007/0142833 A1 | 6/2007 | Dycus et al. | |
| 2007/0142834 A1 | 6/2007 | Dumbauld | |
| 2007/0156139 A1 | 7/2007 | Schechter et al. | |
| 2007/0156140 A1 | 7/2007 | Baily | |
| 2007/0173811 A1 | 7/2007 | Couture et al. | |
| 2007/0173814 A1 | 7/2007 | Hixson et al. | |
| 2007/0179499 A1 | 8/2007 | Garrison | |
| 2007/0198011 A1 | 8/2007 | Sugita | |
| 2007/0203485 A1 | 8/2007 | Keppel | |
| 2007/0213706 A1 | 9/2007 | Dumbauld et al. | |
| 2007/0213707 A1 | 9/2007 | Dumbauld et al. | |
| 2007/0213708 A1 | 9/2007 | Dumbauld et al. | |
| 2007/0213712 A1 | 9/2007 | Buysse et al. | |
| 2007/0255279 A1 | 11/2007 | Buysse et al. | |
| 2007/0260235 A1 | 11/2007 | Podhajsky | |
| 2007/0260238 A1 | 11/2007 | Guerra | |
| 2007/0260241 A1 | 11/2007 | Dalla Betta et al. | |
| 2007/0260242 A1 | 11/2007 | Dycus et al. | |
| 2007/0265616 A1 | 11/2007 | Couture et al. | |
| 2008/0004616 A1 | 1/2008 | Patrick | |
| 2008/0009860 A1 | 1/2008 | Odom | |
| 2008/0015575 A1 | 1/2008 | Odom et al. | |
| 2008/0021450 A1 | 1/2008 | Couture | |
| 2008/0033428 A1 | 2/2008 | Artale et al. | |
| 2008/0039835 A1 | 2/2008 | Johnson et al. | |
| 2008/0039836 A1 | 2/2008 | Odom et al. | |
| 2008/0045947 A1 | 2/2008 | Johnson et al. | |
| 2008/0058802 A1 | 3/2008 | Couture et al. | |
| 2008/0082100 A1 | 4/2008 | Orton et al. | |
| 2008/0091189 A1 | 4/2008 | Carlton | |
| 2008/0114356 A1 | 5/2008 | Johnson et al. | |
| 2008/0167651 A1 | 7/2008 | Tetzlaff et al. | |
| 2008/0195093 A1 | 8/2008 | Couture et al. | |
| 2008/0215051 A1 | 9/2008 | Buysse et al. | |
| 2008/0243120 A1 | 10/2008 | Lawes et al. | |
| 2008/0249527 A1 | 10/2008 | Couture | |
| 2008/0312653 A1 | 12/2008 | Arts et al. | |
| 2008/0319442 A1 | 12/2008 | Unger et al. | |
| 2009/0012520 A1 | 1/2009 | Hixson et al. | |
| 2009/0018535 A1 | 1/2009 | Schechter et al. | |
| 2009/0024126 A1 | 1/2009 | Artale et al. | |
| 2009/0043304 A1 | 2/2009 | Tetzlaff et al. | |
| 2009/0048596 A1 | 2/2009 | Shields et al. | |
| 2009/0062794 A1 | 3/2009 | Buysse et al. | |
| 2009/0082766 A1 | 3/2009 | Unger et al. | |
| 2009/0082767 A1 | 3/2009 | Unger et al. | |
| 2009/0082769 A1 | 3/2009 | Unger et al. | |
| 2009/0088738 A1 | 4/2009 | Guerra et al. | |
| 2009/0088739 A1 | 4/2009 | Hushka et al. | |
| 2009/0088740 A1 | 4/2009 | Guerra et al. | |
| 2009/0088741 A1 | 4/2009 | Hushka et al. | |
| 2009/0088744 A1 | 4/2009 | Townsend | |
| 2009/0088745 A1 | 4/2009 | Hushka et al. | |
| 2009/0088746 A1 | 4/2009 | Hushka et al. | |
| 2009/0088747 A1 | 4/2009 | Hushka et al. | |
| 2009/0088748 A1 | 4/2009 | Guerra et al. | |
| 2009/0088749 A1 | 4/2009 | Hushka et al. | |
| 2009/0088750 A1 | 4/2009 | Hushka et al. | |
| 2009/0112206 A1 | 4/2009 | Dumbauld et al. | |
| 2009/0131934 A1 | 5/2009 | Odom et al. | |
| 2009/0149853 A1 | 6/2009 | Shields et al. | |
| 2009/0149854 A1 | 6/2009 | Cunningham et al. | |
| 2009/0171350 A1 | 7/2009 | Dycus et al. | |
| 2009/0171353 A1 | 7/2009 | Johnson et al. | |
| 2009/0182327 A1 | 7/2009 | Unger | |
| 2009/0187188 A1 | 7/2009 | Guerra et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0541930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |

| | | |
|---|---|---|
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| RU | SU401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 A | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/067798 A1 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO 2004/052221 | 6/2004 |
| WO | WO 2004/073488 A2 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | 2005/004734 A1 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger. Washington University School of Medicine, St. Louis MO, Presented at AHPBA. Feb. 2001.
Johnson et al. "Evaluation of the LigaSure Vessel Sealing System in Hemorrhoidectomy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001, pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium and Large-Sized Arteries" Carolinas Laparoscopic and Advance Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work,Sep. 1999.

Herman et al., "Laparoscopic Intestinal Resection With the LigaSure Vessel Sealing System: A Case Report" Innovations That Work,Feb. 2002.

Carus et al., "Initial Experience With the LigaSure Vessel Sealing System in Abdominal Surgery" Innovations That Work,Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales/Product Literature 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04013772 dated Apr. 1, 2005.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 1683496 dated Jun. 13, 2006.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report Extended- EP 07 009029.5 dated Jul. 12, 2007.
Int'l Search Report EP 07 009321.6 dated Aug. 17, 2007.

* cited by examiner

RADIOFREQUENCY FUSION OF CARDIAC TISSUE

CROSS-REFERENCE TO RELATED APPLICATIONS

This application claims the benefit of priority of U.S. Provisional Patent Application No. 60/848,959 by Moses et al., filed on Oct. 3, 2006, entitled "RADIOFREQUENCY FUSION OF CARDIAC TISSUE", the entire contents of which is incorporated by reference herein.

BACKGROUND

1. Technical Field

The present disclosure relates to methods and apparatuses for repairing and/or altering cardiac tissue such as a valve, including valve leaflets such as coapting valve leaflets.

2. Background

Surgical procedures such as heart valve repair and/or replacement are effective in treating heart valve incompetence (regurgitation, insufficiency) and/or damaged heart valves. However, such techniques are problematic in that invasive surgery is required to reach the valves with a surgical instrument. For example, in order to perform mitral valve surgery, a surgeon may be required to make large openings in the chest to access the mitral valve through a left atriotomy. Further, one or more large openings in the chest may be needed to cannulate the aorta and vena cavae to manipulate surgical instruments, to stop the heart during a cardiac procedure, and to repair or replace a heart valve. Such procedures result in significant trauma and metabolic derrangment to the patient and may not be appropriate for some patients such as the elderly, or patients with significant cardiac disease and/or other diseased states.

Currently, open surgical repair of damaged or incompetent heart valves employs a variety of techniques including annuloplasty rings, excision of damaged or prolapsing leaflets, transfer of chordae tendinae, artificial chordae tendinae, and edge-to-edge leaflet repair. Some of these methods for open surgical heart valve repair may be amendable to less invasive approaches such as beating heart surgery, minimally invasive surgery, thorascopic surgery, or endovascular approaches. One technique for open surgical valve repair in particular, known as the Alferi or edge-to-edge repair, might be accomplished by less invasive approaches. The edge-to-edge repair involves the fusion of opposing (facing) valve leaflets to correct valve incompetence secondary to leaflet prolapse. Current methods for edge-to-edge repair employ either classic surgical suturing with suture materials or surgical staples to accomplish leaflet fusion.

SUMMARY

The present disclosure relates to methods for fusing and/or sealing, adhering or binding heart valve leaflets or portions thereof together with or without opening the chest of a patient, with or without opening or stopping the heart, and/or with or without cardiopulmonary bypass (i.e., open-heart surgery). Such methods include the step of providing a forceps having at least one shaft and an end effector assembly attached thereto. The end effector assembly includes a pair of opposing jaw members configured to move from an open, spread position to a closed, grasping position. The method also includes the steps of creating at least one opening in the patient for inserting the forceps therein and inserting the forceps through the at least one opening to gain access to the cardiac chambers and heart valves. The method also includes the steps of manipulating the jaw members of the forceps through the at least one opening to grasp a portion of a first heart valve leaflet and a portion of a second heart valve leaflet therebetween; activating the forceps to close the jaw members about the leaflet portions under a working pressure sufficient to fuse or seal the first heart valve leaflet to the second heart valve leaflet when radiofrequency energy is applied to the jaw members; and applying radiofrequency energy to the jaw members to fuse or seal the portion of the first heart valve leaflet to the portion of the second heart valve leaflet.

In some embodiments, the at least one opening may be created in at least one of the left femoral artery, the right femoral artery, left femoral vein and right femoral vein. At least one opening may be created into the patient's chest through at least one intercostal space, sternum, diaphragm, or thoracic inlet into the pleural space or mediastinal space. In one embodiment, at least one opening is created through at least a portion of one ventricle and/or one atrium. The method may further include the step of introducing a viewing scope at least partially through the at least one opening. In one embodiment, each jaw member may include an electrically conductive sealing plate adapted to connect to an energy source and configured to communicate energy through tissue held therebetween. At least one of the electrically conductive sealing plates may include at least one stop member disposed thereon for controlling the gap distance between the jaw member within the range of about 0.001 inches (about 0.025 millimeters) to about 0.006 inches (about 0.152 millimeters), or preferably about 0.002 inches (about 0.051 millimeters) to about 0.010 inches (about 0.254 millimeters) for large tissue structures.

The present disclosure relates particularly to a method for treating mitral valve incompetence or regurgitation by fusing or sealing the anterior and posterior mitral valve leaflets within the chest of a patient. The method includes the steps of creating an opening in the patient for inserting a radiofrequency device into the heart of the patient; inserting the radiofrequency device within the opening; engaging a first portion of a mitral valve leaflet and a second portion of the mitral valve leaflet between a pair of jaw members of the radiofrequency device; closing the jaw members under a working pressure; and applying radiofrequency energy to the jaw members to seal the first portion and the second portion of the mitral valve leaflet. The method may be implemented wherein each jaw member includes an electrically conductive sealing plate adapted to connect to an energy source and configured to communicate energy through tissue held therebetween. At least one of the electrically conductive sealing plates may include at least one stop member disposed thereon for controlling the gap distance between said jaw member within the range of about 0.001 inches (about 0.025 millimeters) to about 0.006 inches (about 0.152 millimeters). Other gap distance ranges are also contemplated for large tissue structures, e.g., from about 0.002 inches (0.051 millimeters) to about 0.010 inches (about 0.254 millimeters).

These and other aspects of this disclosure will be evident upon reference to the following detailed description.

DETAILED DESCRIPTION

Methods in accordance with the present disclosure seal, fuse, repair and/or alter one or more portions of a valve together to fix a valve and/or reduce valve regurgitation. As used herein, the terms "seal" and "fuse" or "sealing" and "fusing" or "sealed" and "fused" are used interchangeably as being equivalent. The foregoing terms are defined herein also as referring normally only to partial sealing or fusing of heart valve leaflets, as opposed to complete sealing or fusing of the same, but are not limited in either respect.

Figure 1:
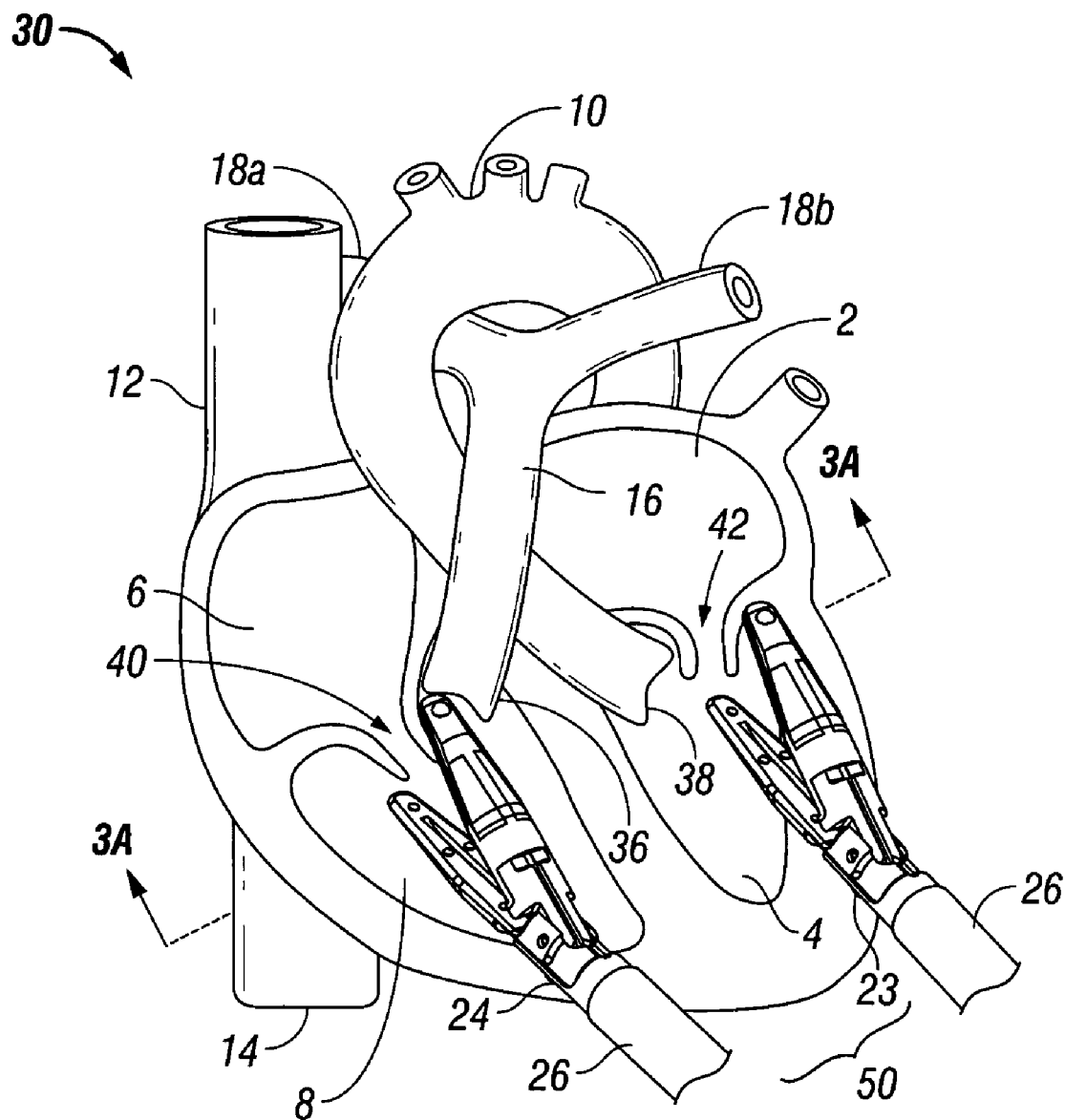
FIG. 1 is a cross-section view of the heart showing an approach for a radiofrequency device either to the mitral valve in the left ventricle or to the tricuspid valve in the right ventricle in accordance with one embodiment of the present disclosure.

Referring now to FIG. 1, a heart 30 is illustrated in a cut-away anterior view illustrating the left atrium 2 and left ventricle 4, with mitral valve 42 disposed therebetween to allow blood (not shown) to move from the left atrium 2 into the left ventricle 4, and also illustrating the right atrium 6 and right ventricle 8, with tricuspid valve 40 disposed therebetween to allow blood (not shown) to move from the right atrium 6 into the right ventricle 8. As discussed below with respect to FIG. 3A, the heart 30 also includes the aortic valve 38 that allows the blood to move out of the left ventricle 4 via the aortic arch 10 to flow to the body (not shown) and the pulmonary valve 36 that allows the blood, flowing from the body via the superior vena cava 12 and inferior vena cava 14, to move from the right ventricle 8 to the lungs (not shown) via the pulmonary trunk 16 leading to the right and left pulmonary arteries 18a and 18b, respectively. An endoscopic radiofrequency device 26 is also visible, which in this embodiment is disposed in an open configuration, approaching the mitral valve 42 prior to sealing, fusing, repairing and/or altering one or more portions of the mitral valve 42 together to treat the mitral valve 42 and/or reduce mitral valve 42 regurgitation. In addition, endoscopic radiofrequency device 26 is also shown disposed in an open configuration approaching the tricuspid valve 40 prior to sealing, fusing, repairing and/or altering one or more portions of tricuspid valve 40 together to treat tricuspid valve 40 and/or reduce tricuspid valve 40 regurgitation.

Figure 2:
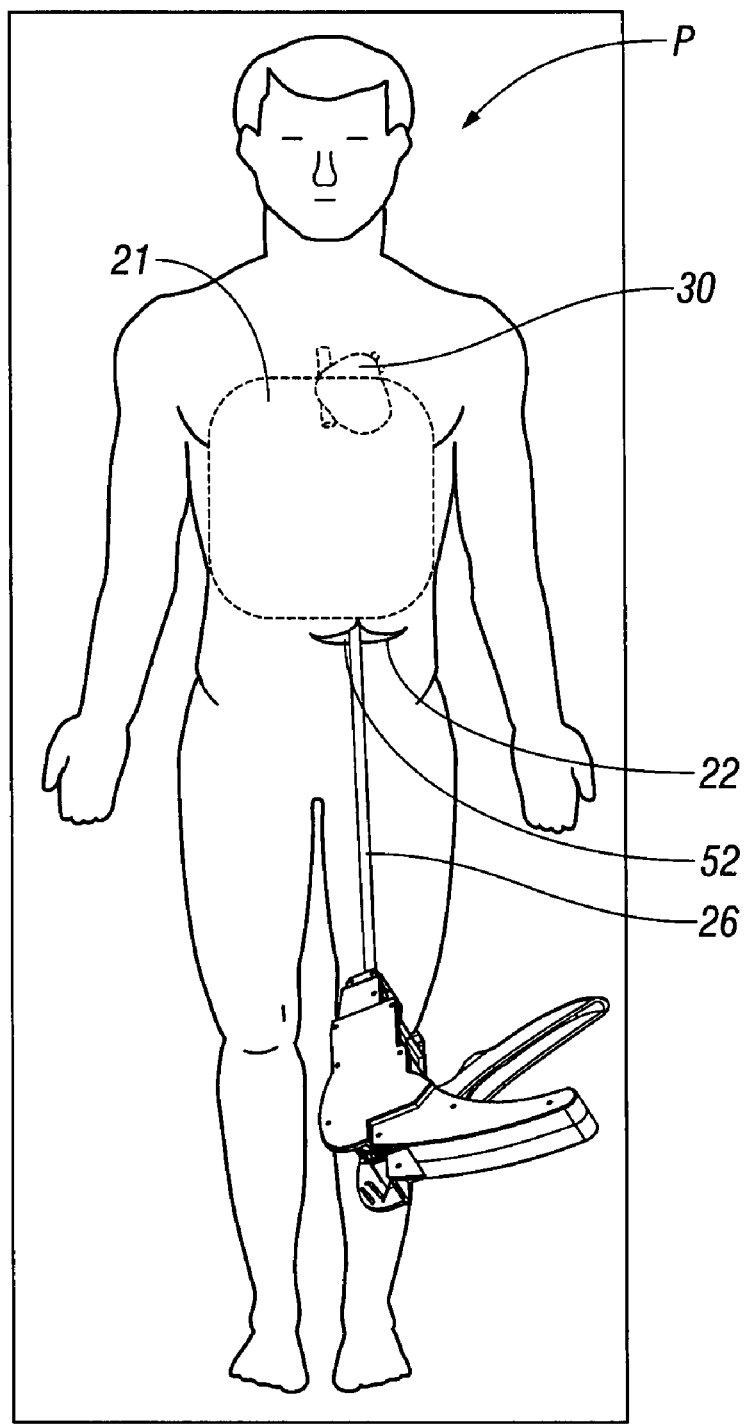
FIG. 2 is a front view of a patient, showing an incision and an opening in the diaphragm for a radiofrequency device in accordance with one embodiment of the present disclosure.

Referring also to FIG. 2, patient "P" is undergoing valve repair in accordance with an embodiment of the present disclosure, which may require an incision 22. A small incision 22 may be made in the diaphragm 52 of the patient "P" to insert the radiofrequency device 26 for mitral valve repair. The incision or opening may be about 0.5 (about 1.27 centimeters) to about 5 inches (about 12.7 centimeters) in length. After initial incision of the skin, one or more suitable medical devices may be used to navigate a path between the skin incision 22 and the heart 30 of the patient "P". For example, imaging devices, such as an angioscope, as well as cutting and/or suturing devices may be used. Imaging devices may be placed in or on the patient to monitor the procedure. Medical devices, such as cutting and/or suturing devices may then be used to make at least one opening in a ventricle and/or atrium, including the left ventricle and left atrium. For example, opening 23 in left ventricle 4 provides direct access to the mitral valve 42 while opening 24 in right ventricle 8 provides direct access to the tricuspid valve 40 (see FIG. 1). Any suitable access methods or devices may be used to gain surgical access to the mitral valve 42, or other valve or tissue to be repaired. Methods in accordance with the present disclosure may be performed on a beating heart, thus eliminating the need for cardiopulmonary bypass. However, many embodiments may also be suitable for use in open-heart surgery techniques and/or in conjunction with use of cardiopulmonary bypass. Alternatively, some devices and methods may use one or more blood vessels to obtain access to the heart by catheterization, transvenous, or transarterial approaches. The chest 21 of the patient "P" may be open or closed depending on the devices and methods to be used for the sealing, fusing, fixing, repairing and/or altering of the heart valve tissue.

In embodiments, the heart valve such as the mitral valve 42 is accessed and the methods are applied from the ventricular side of the valve 42, or within the left ventricle 4. For example, given the anatomy and shape of the mitral valve 42, it may be difficult to apply techniques in accordance with the present disclosure from the atrial side of the heart 30, i.e., from the left atrium 2 or the right atrium 6. Accordingly, devices suitable for use with methods in accordance with the present disclosure may be passed through the apex 50 of the ventricles 4 and 8. In embodiments, such as catheter-based applications, a medical device may be passed through the femoral artery (not shown), through the aortic valve 38 into the left ventricle 4 or through a femoral vein (not shown) across the atrial septum and through the mitral orifice to fuse, seal, fix, repair and/or treat the mitral valve 42 from the ventricular side.

Figure 3A:
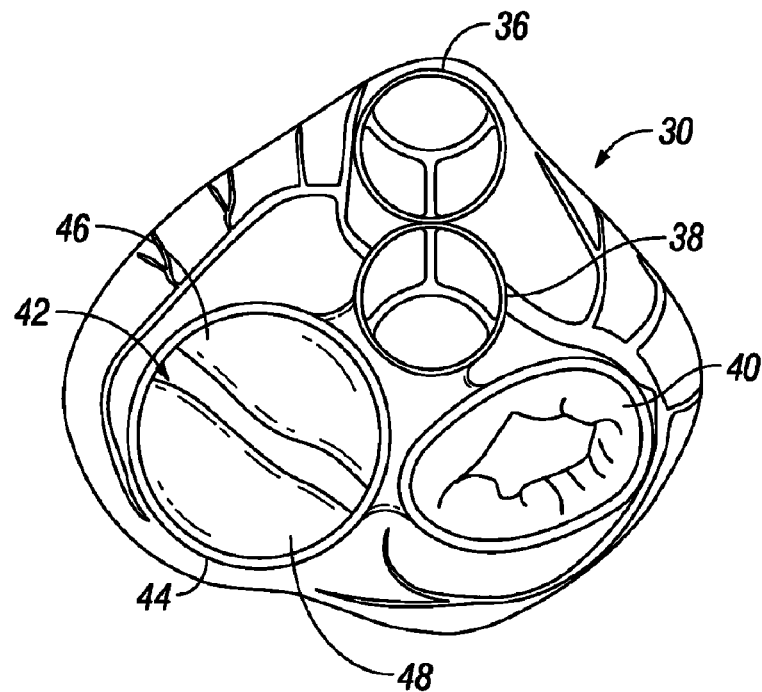
FIG. 3A is a cut-away view of a heart, viewed from the base of the heart taken along section 3A-3A of FIG. 1, with the atria cut away to view the valves, with a mitral valve prior to repair in accordance with an embodiment of the present disclosure.
Figure 3B:
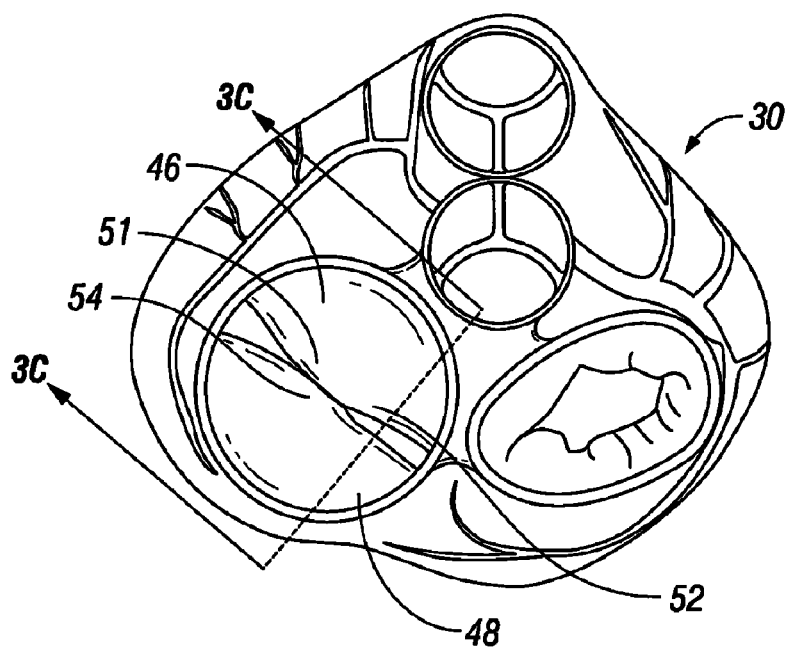
FIG. 3B is a cut-away view of a heart, viewed from the base of the heart, with the atria cut away to view the valves, while the mitral valve is being repaired in accordance with an embodiment of the present disclosure.

Referring now to FIGS. 3A-3B, heart 30 is viewed from the perspective of the base of the heart 30 (roughly, the top or cephalic part of the heart), as if the right and left atria 6 and 2, respectively, were removed. The pulmonary 36, aortic 38, tricuspid 40 and mitral 42 valves are shown, as well as the mitral valve annulus 44 and the anterior leaflet 46 and posterior leaflet 48 of mitral valve 42.

Figure 3C:
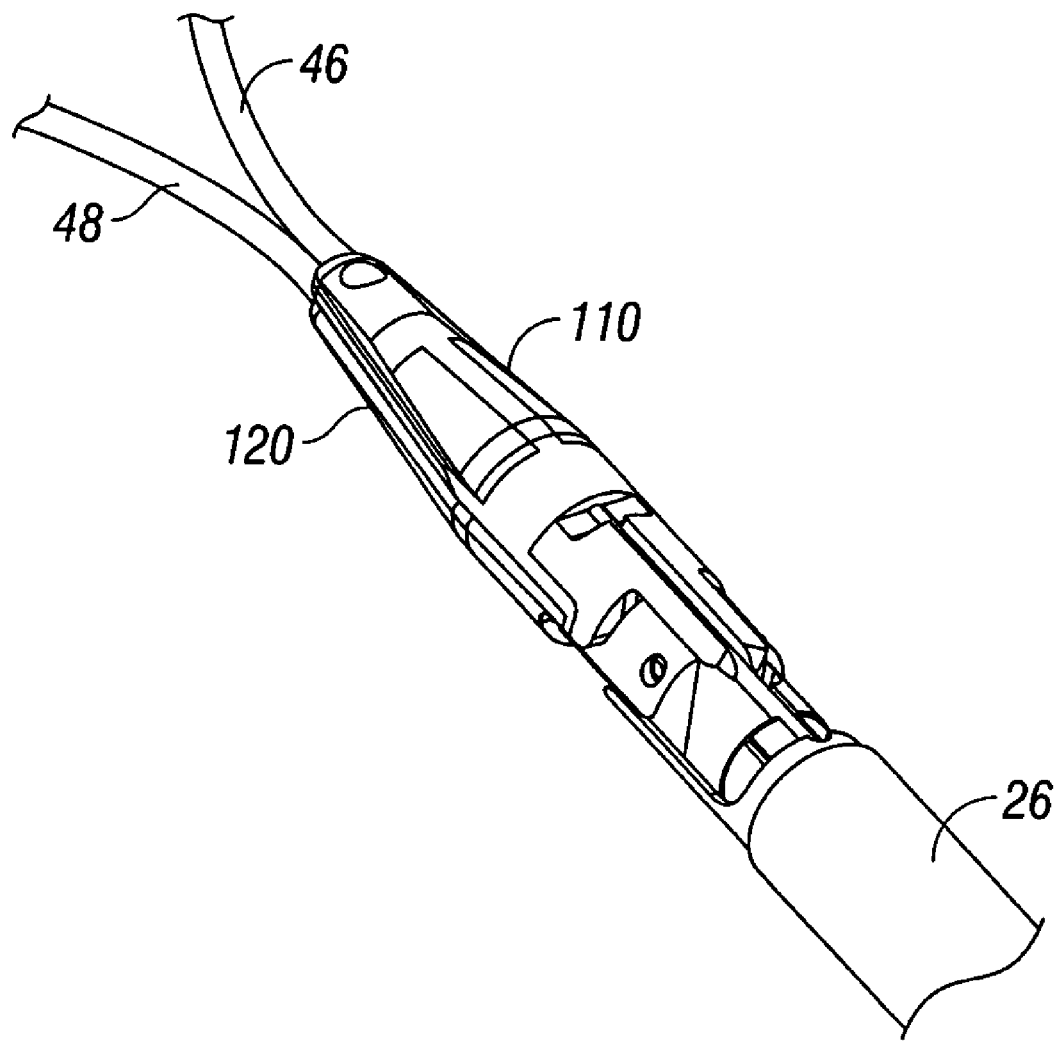
FIG. 3C is a view along section 3C-3C of FIG. 3B showing a radiofrequency device in a closed position for mitral valve repair.

Referring also to FIG. 3C, radiofrequency device 26 contacts with at least one heart valve leaflet 46, 48. More particularly, the jaw members 110 and 120 of end effector assembly 100 of radiofrequency device 26 contact at least two portions of heart valve leaflet 46, 48 to create a treatment site 51 where a first portion 52 of heart valve leaflet 46 and a second portion 54 (see FIG. 3B) of heart valve leaflet 48 are adjacent to one another.

Radiofrequency device 26 is suitable for applying radiofrequency energy and/or pressure to the treatment site in amounts sufficient to seal or fuse the first portion 52 of heart valve leaflet 46 to the second portion of heart valve leaflet 48. For example, electrical energy in the frequency range of 300 kilohertz (kHz) to 1 megahertz (MHz) may be directly applied to one or more treatment sites 51 in amounts sufficient to seal or fuse the first portion of heart valve leaflet 46 to the second portion of heart valve leaflet 48. In addition, radiofrequency device 26 may be configured to provide pressure in amounts sufficient to effectively seal or fuse the first portion of heart valve leaflet 46 to the second portion of heart valve leaflet 48 at one or more treatment sites 51.

Figure 3D:
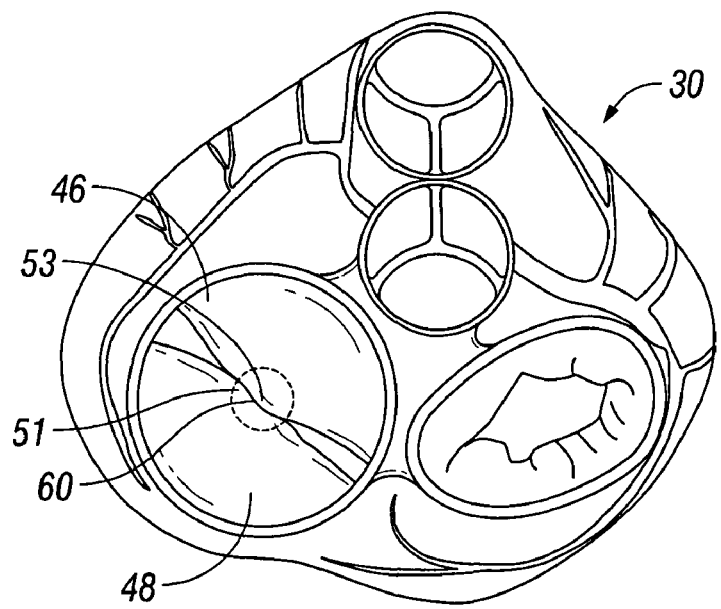
FIG. 3D is a cut-away view of a heart, viewed from the base of the heart, with the atria cut away to view the valves, and a fused mitral valve repaired in accordance with the method according to an embodiment of the present disclosure.

Referring now to FIG. 3D, treatment site 51 is shown having a site of leaflet fusion, seal, adhesion or weld 60 where heart leaflet 46 and heart leaflet 48 are sealed or fused together. As used herein, sealing, fusion, fixation or adhesion refer to the process of liquefying the tissues and ground substances in the tissues so that they reform into a fused mass with significantly reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them. Larger vessels and cardiac tissue need to be "sealed" or "fused" to assure a permanent weld. In some embodiments, treatment site 51 is positioned in or around the middle of the two heart valve leaflets 46 and 48 such that the middle portion of the mitral valve 42 is treated with a radiofrequency device, e.g., radiofrequency device 26, in accordance with the present disclosure. Referring to FIG. 3D, heart valve leaflets 46, 48 are sealed or fused together at treatment site 51, which is near the middle of leaflets 46, 48. In other embodiments (not shown), the leaflet fusion site might be offset towards one of the valve commissures.

Figure 3E:
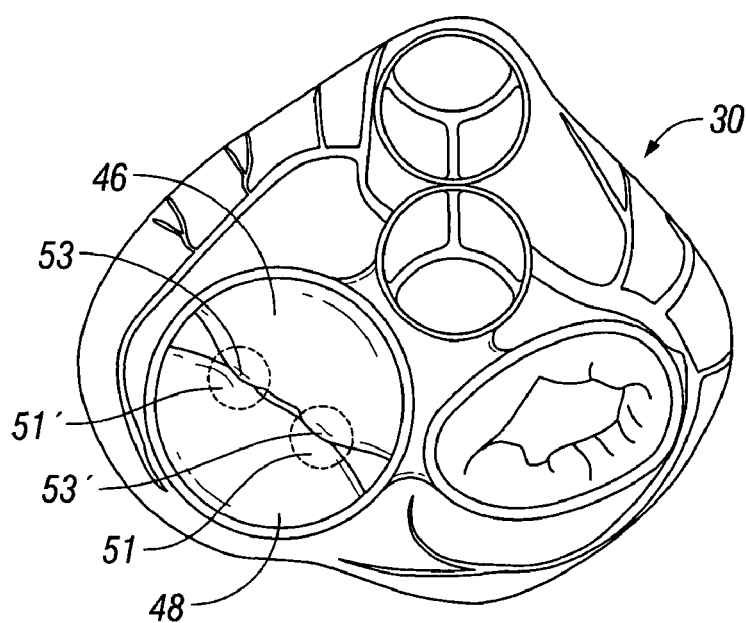
FIG. 3E is a cut-away view of a heart, viewed from the base of the heart, with the atria cut away to view the valves, and a mitral valve fused at two treatment sites in accordance with one particular method according to an embodiment of the present disclosure.

Referring to FIG. 3E, two seals 53, 53' are shown that were formed by methods in accordance with the present disclosure. In some embodiments, at least two treatment sites such as 51, 51' are treated with a radiofrequency device, e.g., radiofrequency device 26, in accordance with the present disclosure. Referring to FIG. 3E, heart valve leaflets 46, 48 are fused or sealed together at two treatment sites 51, 51'. In some embodiments, a surgeon can apply a plurality of fusions or seals to one or more tissues, such as mitral valve leaflets. For example, the surgeon, upon having access to the heart 30, may freely position the radiofrequency device 26 at a plurality of treatment sites and activate the device 26 in accordance with the present disclosure to create a plurality of fusions or seals.

Figure 3F:
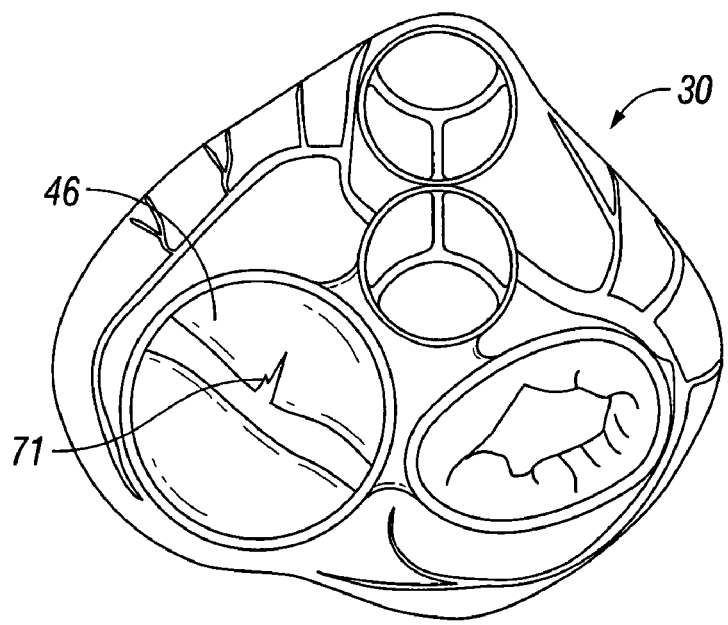
FIG. 3F is a cut-away view of a heart, viewed from the base of the heart, with the atria cut away to view the valves, and a mitral valve in need of repair.
Figure 3G:
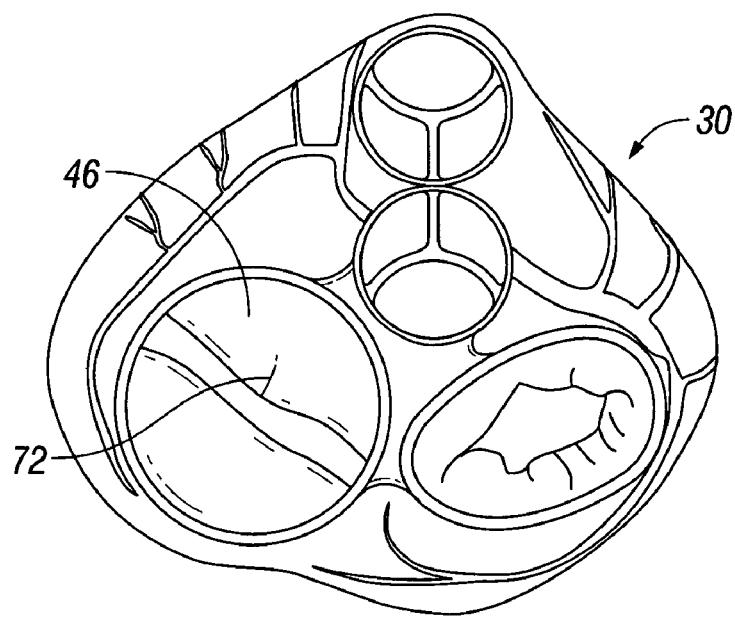
FIG. 3G is a cut-away view of a heart, viewed from the base of the heart, with the atria cut away to view the valves, and the mitral valve of FIG. 3F repaired in accordance with a particular method of the present disclosure.

Referring to FIG. 3F, a worn heart valve leaflet 46 is shown having a lesion 71 therein. Lesion 71 is problematic in that it prevents the mitral valve 42 from functioning normally and allows blood to incorrectly flow backwards into the atrium 2 when the heart 30 is pumping. In some embodiments, a surgeon may use methods in accordance with the present disclosure to seal lesion 71 and improve the performance of leaflet 46. For example, through catheterization, a surgeon can apply the radiofrequency device 26 to the leaflet of a beating heart and treat lesions or worn valves or components thereof. FIG. 3G shows the heart 30 of FIG. 3F after application of a radiofrequency device, e.g., radiofrequency device 26, in accordance with the present disclosure to seal lesion 71. The tissue 72 has fused and the performance of the leaflet is improved.

Figure 4A:
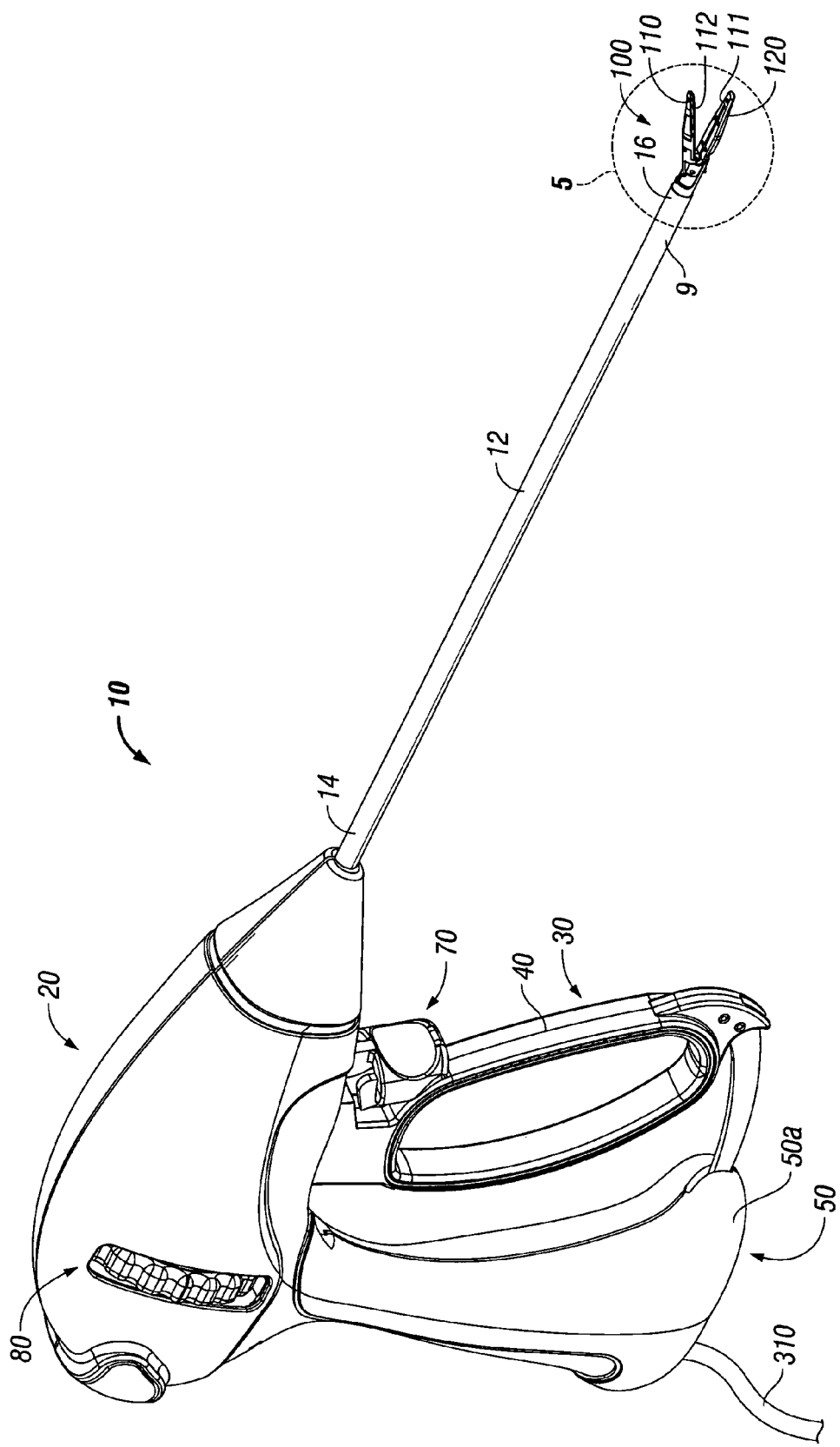
FIG. 4A is a perspective view of an endoscopic bipolar forceps suitable for use with a particular method of the present disclosure.
Figure 4B:
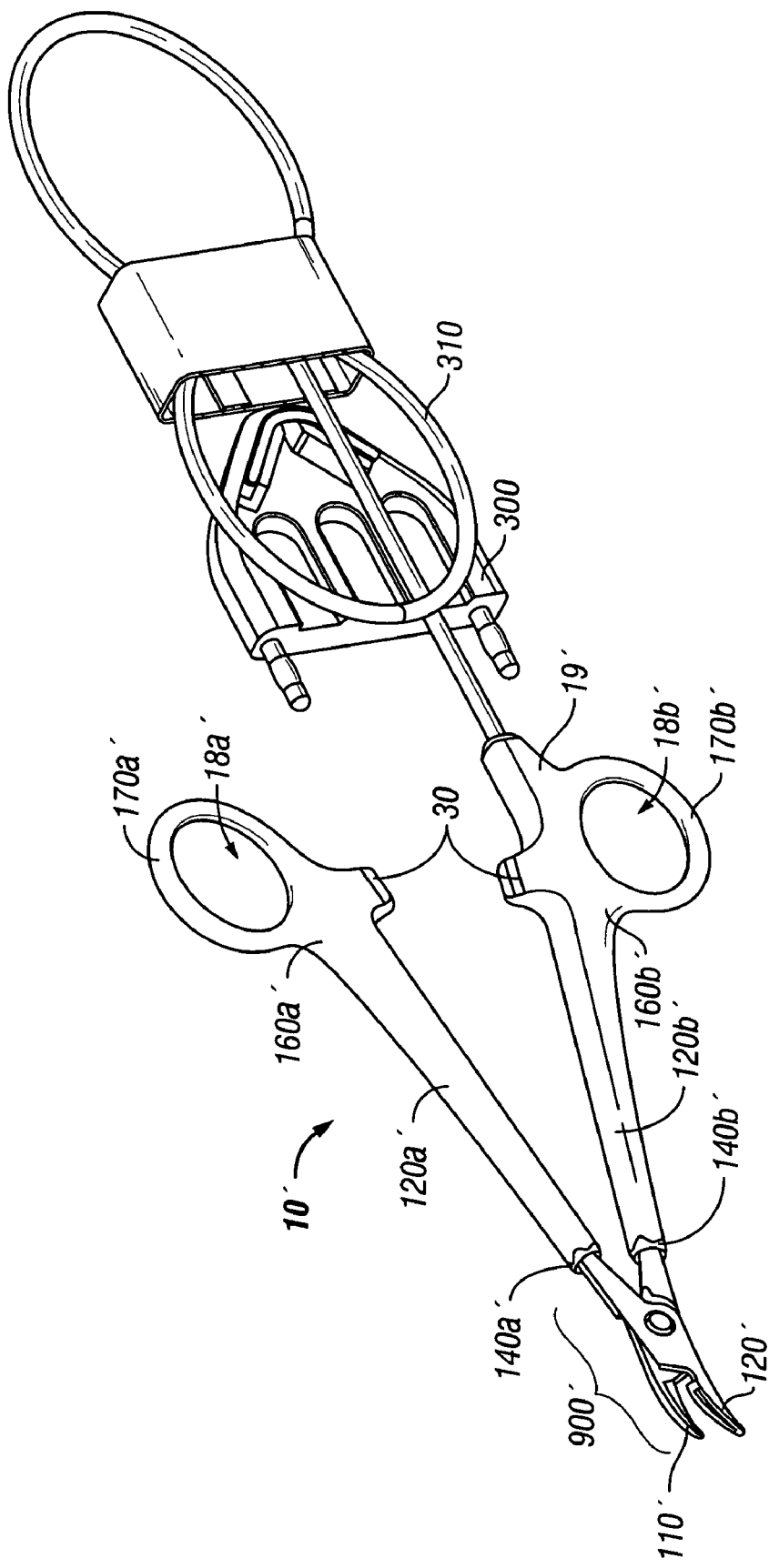
FIG. 4B is a perspective view of an open bipolar forceps suitable for use with a particular method of the present disclosure.

Referring now to FIG. 4A and FIG. 4B, two bipolar forceps 10 and 10', respectively, are shown; a first forceps 10 may be used with endoscopic surgical procedures and a second forceps 10' for use with open surgical procedures. An endoluminal device (not shown), may also be utilized for the purposes herein. For the purposes herein, either an endoscopic instrument or an open instrument may be utilized for radiofrequency procedures in accordance with the present disclosure. Obviously, different electrical and mechanical connections and considerations apply to each particular type of instrument; however, the novel aspects with respect to the sealing, fusing, repairing and/or altering cardiac tissue such as a valve, and its operating characteristics remain generally consistent with respect to the endovascular, endoscopic or open designs of FIGS. 4A and 4B, respectively. Forceps 10 and 10' are shown by way of example and other electrosurgical forceps are also envisioned that may support the methods in accordance with the present disclosure. In the drawings and in the description that follows, the term "proximal", as is traditional, will refer to the end of the forceps 10, 10' that is closer to the user, while the term "distal" will refer to the end that is further from the user.

FIG. 4A shows one example of an endoscopic vessel sealing instrument 10 which is configured to seal, repair and/or alter cardiac tissue such as a valve. More particularly, forceps 10 generally includes a housing 20, a handle assembly 50, a rotating assembly 80, a trigger assembly 70 and the end effector assembly 100 which mutually cooperate to grasp, seal and, if warranted, divide tissue. The forceps 10 includes a shaft 12 which has a distal end 9 dimensioned to mechanically engage the end effector assembly 100 and a proximal end 14 which mechanically engages the housing 20 proximate the rotating assembly 80.

Forceps 10 also includes a plug (not explicitly shown) which connects the forceps 10 to a source of electrosurgical energy, e.g., an electrosurgical generator (not shown) via an electrical cable 310. Handle assembly 50 includes a fixed handle 50a and a movable handle 40. Handle 40 moves relative to fixed handle 50 to actuate the end effector assembly 100 and enable a user to grasp and manipulate cardiac tissue such as a valve. More particularly, the end effector assembly 100 includes a pair of opposing jaw members 110 and 120 which move in response to movement of the handle 40 from an open position wherein the jaw members 110 and 120 are disposed in spaced relation relative to one another, to a clamping or closed position wherein the jaw members 110 and 120 cooperate to grasp tissue therebetween.

The housing 20 encloses a drive assembly (not shown in FIG. 4A) which cooperates with the movable handle 40 to impart movement of the jaw members 110 and 120 from the open position to the clamping or closed position. The handle assembly 30 can generally be characterized as a four-bar mechanical linkage which provides a unique mechanical advantage when fusing or sealing tissue between the jaw members 110 and 120. For example, once the desired position for the fusing or sealing site is determined and the jaw members 110 and 120 are properly positioned, handle 40 may be compressed fully to lock the jaw members 110 and 120 in a closed position against the tissue. Further, should it be determined that tissue should be divided, trigger assembly 70 may be compressed to actuate a blade assembly (not explicitly shown) located in the end effector assembly 100. Other force activating assemblies and trigger mechanisms are envisioned which may be used in connection with the blade assemblies described herein. The details relating to the inter-cooperative relationships of the inner-working components of various forceps 10 are disclosed in commonly-owned U.S. patent application Ser. No. 10/284,562, U.S. patent application Ser. No. 10/460,926, and U.S. patent application Ser. No. 10/369,894. When the jaw members 110 and 120 are fully compressed about the tissue, the forceps 10 is now ready for selective application of electrosurgical energy and/or tissue fusion, repair and/or alteration.

The gap distance between jaw members must be regulated to assure a consistent and reliable seal. At least one of the jaw members includes one or more stop members on a conductive surface thereof which regulates the gap distance to about 0.001 inches (about 0.025 millimeters) to about 0.006 inches (about 0.152 millimeters). Other gap distance ranges are also contemplated for large tissue structures, e.g., from about 0.002 inches (about 0.051 millimeters) to about 0.010 inches (about 0.254 millimeters).

Figure 5:
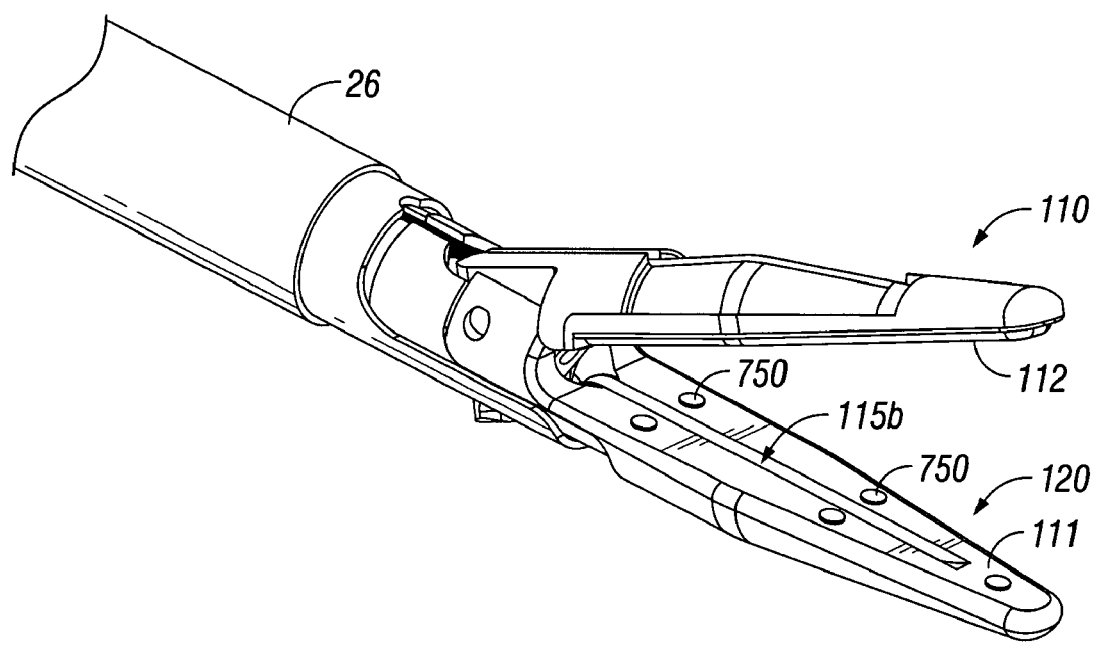
FIG. 5 is a greatly enlarged view of the end effector assembly of the forceps shown in FIG. 4A.

As best seen in FIG. 5, jaw member 120 includes a series of stop members 750 preferably disposed on the inner facing surfaces of the electrically conductive sealing surface 111 to facilitate gripping and manipulation of tissue and to define a gap between opposing jaw members 110 and 120 during sealing, fusing, repairing and/or altering of cardiac tissue such as heart valve leaflets. It is envisioned that the series of stop members 750 may be employed on one or both jaw members 110 and 120 depending upon a particular purpose or to achieve a desired result. A detailed discussion of these and other envisioned stop members 750 as well as various manufacturing and assembling processes for attaching and/or affixing the stop members 750 to the electrically conductive sealing or fusing surfaces 111, 112 are described in commonly-assigned, co-pending U.S. application Ser. No. 10/471,818 entitled "VESSEL SEALER AND DIVIDER WITH NON-CONDUCTIVE STOP MEMBERS" by Dycus et al.

An open forceps 10' for use in connection with traditional open surgical procedures is shown by way of example in FIG. 4B. Open forceps 10' includes a pair of elongated shaft portions 120a', 120b' each having a proximal end 160a' and 160b', respectively, and a distal end 140a' and 140b', respectively. The forceps 10' includes jaw assembly 900' which attaches to the distal ends 140a' and 140b' of shafts 120a' and 120b', respectively. Jaw assembly 900' includes an upper jaw member 110' and a lower jaw member 120' which are movable relative to one another to grasp tissue therebetween.

Still referring to FIG. 4B, each shaft 120a' and 120b' includes a handle 170a' and 170b'disposed at the proximal end 160a' and 160b' thereof which each define a finger hole 180a' and 180b', respectively, therethrough for receiving a finger of the user. As can be appreciated, finger holes 18a' and 18b' facilitate movement of the shafts 120a' and 120b' relative to one another which, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

A ratchet 30 is included for selectively locking the jaw members 110' and 120' relative to one another at various positions during pivoting. In embodiments, each position associated with the cooperating ratchet interfaces 30 holds a specific, i.e., constant, strain energy in the shaft members 120a' and 120b' which, in turn, transmits a specific closing force to the jaw members 110' and 120'. It is envisioned that the ratchet 30 may include graduations or other visual markings which enable the user to easily and quickly ascertain and control the amount of closure force desired between the jaw members 110' and 120'. One of the shafts, e.g., 120b', includes a proximal shaft connector/flange 19' which is designed to connect the forceps 100' to a source of RF energy (not shown) via an electrosurgical cable 310 and plug 300. The details relating to the inner-working electrical connections and various envisioned forceps 10' are disclosed in commonly-owned U.S. patent application Ser. No. 10/962,166, U.S. patent application Ser. No. 10/991,157, and U.S. patent application Ser. No. 10/873,860.

As mentioned above, two mechanical factors play an important role in determining the resulting thickness of the fused or sealed tissue and effectiveness of the fusion or seal, i.e., the pressure applied between opposing jaw members 110' and 120' and the gap (about 0.001 to about 0.006 inches, or about 0.025 to about 0.152 millimeters) between the opposing jaw members 110' and 120' during the fusing or sealing process. Other gap distance ranges are also contemplated for large tissue structures, e.g., from about 0.002 inches (0.051 millimeters) to about 0.010 inches (about 0.254 millimeters). Applying the correct force is also important for other reasons: to reduce the impedance of the tissue to a low enough value that allows enough current through the tissue; and to overcome the forces of expansion during the heating of the tissue in addition to contributing towards creating the required fusion or seal thickness necessary for a good fusion or seal.

For the purposes herein, electrode assemblies 100 and 900' include the same general configuration and are designed so that surgeons can more readily and more easily produce consistent, high quality tissue transections while limiting movement of the end effector assembly. By controlling the intensity, frequency and duration of the RF energy applied to the tissue, the user can selectively seal the tissue as needed for a particular purpose. As can be appreciated, different tissue types and the physical characteristics associated with each tissue type may require different electrical fusing or sealing and/or cutting parameters.

The present methods in accordance with the present disclosure may be applied to any blood vessel to treat tissue therein. As used herein, the word "treat," "treating" or "treatment"refers to using the methods of the present disclosure prophylactically to prevent any undesirable conditions, or therapeutically to ameliorate an existing undesirable condition. A number of different treatments are now possible, which reduce and/or eliminate undesirable conditions.

As used herein, "undesirable condition" refers to any detectable tissue manifestations that require surgical intervention. Such manifestations can appear due to a number of factors such as, for example, trauma and/or other diseased or dysfunctional state. Non-limiting examples of such manifestations include stenosis, regurgitation, and/or other forms of tissue abnormality such as a tear or lesion in the heart, and combinations thereof. The listed undesirable conditions are non-limiting and only a portion of the conditions suitable for treatment in accordance with the present disclosure are listed herein.

In some embodiments, methods in accordance with the present disclosure apply pressure and/or radiofrequency energy in an effective amount to improve undesirable conditions. As used herein, "effective amount" refers to an amount of pressure and/radiofrequency energy needed to obtain a positive benefit by sealing or fusing tissue to repair and/or alter tissue including cardiac tissue such as a valve, corresponding valve leaflets, and combinations thereof. The positive benefit can be health-related. In embodiments, the positive benefit is achieved by sealing or fusing tissue to repair and/or alter tissue during heart surgery for heart valve repair and/or replacement.

The positive benefits can reduce, alleviate, or cure regurgitation by sealing or fusing and/or altering the valve structures to allow the valve to close tightly, or to facilitate procedures where a prosthetic ring is inserted to reshape a deformed valve. Accordingly, the positive benefit can be achieved by altering the valve flaps to stop blood from flowing backwards. A positive benefit can be achieved in that the methods in accordance with the present disclosure may be suitable for some patients that otherwise were not suitable surgical candidates. Other positive benefits of the methods in accordance with the present disclosure include lowering the risk of infection during and/or after surgery, decreasing a need for life-long blood thinner medications and/or preserving heart muscle strength.

A positive benefit may be achieved by fusion of the anterior mitral valve leaflet to the posterior mitral valve leaflet. For example, two different leaflets may be joined to one another.

A patient suffering from regurgitation for failure of a mitral valve to close tightly, may be prepared for cardiac surgery in a conventional manner using conventional techniques and procedures. The patient may be anesthetized and ventilated using conventional techniques. The surgeon prepares an opening to the heart by incising the thoracic wall or sternum with a scalpel. The surgeon next obtains access to the mitral valve through a left atriotomy and/or surgical incision through the left ventricle, and locates a worn leaflet. The surgeon performs a surgical procedure that applies radiofrequency energy and/or pressure to the worn leaflet to fuse or seal and/or reshape the leaflet.

During the surgical procedure, the surgeon optionally elects to have the patient's heart beating to perform a conventional beating heart procedure, although the surgeon has a cardiopulmonary bypass (CBP) machine primed and available if it is necessary to convert the beating heart procedure into a conventional stopped heart procedure. In this application, the instrument may be passed through a small incision in the atrium or ventricle using surgical techniques to control hemorrhage while the instrument is passed across the cardiac wall. In this application, visualization of the heart valve or cardiac structure may be obtained by echocardiography or other suitable imaging technologies.

The patient recovers and has no additional regurgitation.

As can be appreciated from the above description, referring to FIGS. 1-5, the method for sealing heart valve leaflets, e.g., anterior leaflet 46 and posterior leaflet 48 of mitral valve 42, within the chest 21 of the patient "P" includes the steps of providing a forceps, e.g., forceps 10 (see FIG. 4A) or forceps 10' (see FIG. 4B), having at least one shaft, e.g., shaft 12 of forceps 10 or shafts 120a' and 120b' of forceps 10', and an end effector assembly attached thereto, e.g., end effector assembly 100 of forceps 10 (see FIG. 4A) or jaw assembly 900' of forceps 10' (see FIG. 4B). The end effector assembly includes a pair of opposing jaw members configured to move from an open, spread position to a closed, grasping position, e.g., jaw members 110 and 120 of forceps 10 in FIGS. 1, 3C, 4A and 5, and jaw members 110' and 120' of forceps 10' in FIG. 4B. The method includes creating at least one opening in the patient for inserting the forceps 10 therein, e.g., openings 23 and 24 in FIG. 1 and incision 22 in the left thorax of the patient "P". The method includes inserting the forceps 10 through the at least one opening, e.g., incision 22 or openings 23 or 24. The method also includes manipulating the jaw members, e.g., jaw members 110 and 120 of the forceps 10, or jaw members 110' and 120' of forceps 10', through the at least one opening, e.g., incision 22 or openings 23 or 24, to grasp a portion of a first heart valve leaflet and a portion of a second heart valve leaflet therebetween, e.g., treatment site 51 of anterior valve leaflet 46 and treatment site 51 of posterior valve leaflet 48. The method also includes activating the forceps, e.g., forceps 10 or 10', to close the jaw members, e.g., jaw members 110 and 120 of the forceps 10, or jaw members 110' and 120' of forceps 10', about the leaflet portions under a working pressure sufficient to fuse the first heart valve leaflet, e.g., anterior valve leaflet 46, to the second heart valve leaflet, e.g., posterior valve leaflet 48, when radiofrequency energy is applied to the jaw members, and applying radiofrequency energy to the jaw members, e.g., jaw members 110 and 120, or 110' and 120', to seal the portion of first heart valve leaflet 46 to the portion of the second heart valve leaflet 48, e.g., treatment site 51 of anterior valve leaflet 46 and treatment site 51 of posterior valve leaflet 48.

In one embodiment, each jaw member, e.g., jaw members 110 and 120 of forceps 10 and jaw members 110' and 120' of forceps 10', includes an electrically conductive sealing or fusing plate, e.g., electrically conductive fusing surface 111 or 112 (see FIGS. 4A and 5) adapted to connect to an energy source and configured to communicate energy through tissue held therebetween. At least one of the electrically conductive plates 111 and 112 includes at least one stop member, e.g., stop member 750 disposed thereon for controlling the gap distance between the jaw members 110 and 120, or 110' and 120', within the range of about 0.001 inches (about 0.025 millimeters) to about 0.006 inches (about 0.152 millimeters). Other gap distance ranges are also contemplated for large tissue structures, e.g., from about 0.002 inches (about 0.051 millimeters) to about 0.010 inches (about 0.254 millimeters).

Referring to FIGS. 1 and 3D, as can also be appreciated from the above description, the present disclosure describes a method of treating mitral valve regurgitation by fusing or sealing cardiac mitral valve leaflets, e.g., anterior valve leaflet 46 and posterior valve leaflet 48, within the chest 21 of the patient "P". The method includes the steps of creating at least one opening, e.g., opening or incision 22 and/or opening 23 in the left ventricle 4 (or opening 24 in the right ventricle 8 for access to for treating the tricuspid valve 40) in the patient "P" for inserting a radiofrequency device, e.g., radiofrequency device 26, into the heart 30 of the patient "P" and inserting the radiofrequency device, e.g., radiofrequency device 26, within the opening, e.g., opening or incision 22 and/or opening 23 in the left ventricle 4 (or opening 24 in the right ventricle 8 for treating the tricuspid valve 40). The method includes also engaging a first portion of a mitral valve leaflet and a second portion of the mitral valve leaflet, e.g., portions 52 and 54 of the mitral valve leaflet, e.g., anterior leaflet 46 or posterior leaflet 48, between a pair of jaw members of the radiofrequency device, e.g., jaw members 110 and 120 of the forceps 10, or jaw members 110' and 120' of forceps 10'. The method includes closing the jaw members, e.g., jaw members 110 and 120 of the forceps 10, or jaw members 110' and 120' of forceps 10', under a working pressure and applying radiofrequency energy to the jaw members to seal the first portion 52 and the second portion 54 of the mitral valve leaflet, e.g. anterior valve leaflet 46 and posterior valve leaflet 48.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodi-

What is claimed is:

1. A method for sealing at least one lesion in at least one heart valve leaflet within the chest of a patient comprising the steps of:
   providing a forceps having at least one shaft and an end effector assembly attached thereto, the end effector assembly including a pair of opposing jaw members configured to move from an open, spread position to a closed, grasping position;
   creating at least one opening in the patient for inserting the forceps therein;
   inserting the forceps through the at least one opening;
   manipulating the jaw members of the forceps through the at least one opening to grasp a first portion of a lesion of a heart valve leaflet and a second portion of the lesion of the heart valve leaflet therebetween;
   activating the forceps to close the jaw members about the lesion portions under a working pressure sufficient to seal the first portion of the lesion to the second portion of the lesion when radiofrequency energy is applied to the jaw members; and
   applying radiofrequency energy to the jaw members to seal the first portion of the lesion to the second portion of the lesion.

2. The method according to claim 1, wherein the at least one opening is created in at least one of the left femoral artery, the right femoral artery, the left femoral vein, the right femoral vein, and combinations thereof.

3. The method according to claim 1, wherein the at least one opening is created through at least a portion of one of a ventricle and an atrium.

4. The method according to claim 1, further comprising the step of introducing a viewing scope at least partially through the at least one opening.

5. The method according to claim 1, wherein the at least one opening is created in the patient's chest through at least one intercostal space, sternum, thoracic inlet, or diaphragm.

6. The method according to claim 1, wherein each jaw member includes an electrically conductive sealing plate adapted to connect to an energy source and configured to communicate energy through tissue held therebetween, at least one of said electrically conductive sealing plates including at least one stop member disposed thereon for controlling a gap distance between said jaw members.

7. A method of treating mitral valve regurgitation by fusing cardiac mitral valve leaflets within the chest of a patient comprising the steps of:
   creating an opening in the patient for inserting a radiofrequency device into the heart of the patient;
   inserting the radiofrequency device within the opening;
   engaging a first portion of a mitral valve leaflet and a second portion of the mitral valve leaflet between a pair of jaw members of the radiofrequency device;
   closing the jaw members under a working pressure; and
   applying radiofrequency energy to the jaw members to seal the first portion and the second portion of the mitral valve leaflet.

8. The method according to claim 7, wherein each jaw member includes an electrically conductive sealing plate adapted to connect to an energy source and configured to communicate energy through tissue held therebetween, at least one of said electrically conductive sealing plates including at least one stop member disposed thereon for controlling a gap distance between said jaw members.

* * * * *